(12) United States Patent
Chang et al.

(10) Patent No.: US 8,440,811 B2
(45) Date of Patent: May 14, 2013

(54) DNA NANOSTRUCTURES THAT PROMOTE CELL-CELL INTERACTION AND USE THEREOF

(75) Inventors: Yung Chang, Tempe, AZ (US); Hao Yan, Chandler, AZ (US)

(73) Assignee: Arizona Board of Regents, a body corporate acting for and on Behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 13/122,482

(22) PCT Filed: Oct. 2, 2009

(86) PCT No.: PCT/US2009/059432
§ 371 (c)(1),
(2), (4) Date: Jul. 26, 2011

(87) PCT Pub. No.: WO2010/040091
PCT Pub. Date: Apr. 8, 2010

(65) Prior Publication Data
US 2011/0275702 A1  Nov. 10, 2011

Related U.S. Application Data

(60) Provisional application No. 61/102,702, filed on Oct. 3, 2008, provisional application No. 61/117,418, filed on Nov. 24, 2008.

(51) Int. Cl.
*C07H 21/04* (2006.01)
*C07H 21/02* (2006.01)

(52) U.S. Cl.
USPC .... 536/24.5; 536/23.1; 536/24.31; 536/24.33

(58) Field of Classification Search .................. None
See application file for complete search history.

(56) References Cited

FOREIGN PATENT DOCUMENTS

| WO | WO2006/124089 | 11/2006 |
|---|---|---|
| WO | WO2007/139849 | 12/2007 |
| WO | WO2008/033848 | 3/2008 |

OTHER PUBLICATIONS

Rinker et al, Self-assembled nanostructures for distance-dependent multivalent ligand-protein binding. Nat Nanotech, 2008, pp. 418-422, vol. 3.
Carter, Bispecific human IgG by design. J Immun Meth, 2001, pp. 7-15, vol. 248.
Chhabra et al, Spatially addressable multiprotein nanoarrays templated by aptamer-tagged DNA nanoarchitectures. J Am Chem Soo, 2007, pp. 10304-10305, vol. 129.
Hung et al, The central role of CD4 T cells in the antitumor immune response. J Exp Med, 1998, pp. 2357-2368, vol. 188.
Lee et al, Immunoregulatory effects of CD4+ T helper subsets in human melanoma. Surgery, 1995, pp. 365-372, vol. 117.
Binyamin et al, Blocking NK cell inhibitory self-recognition promotes antibody-dependent cellular cytotoxicity in a model of anti-lymphoma therapy. J Immunol, 2008, pp. 6932-6401, vol. 180.
McNamara et al, Multivalent 4-1BB binding aptamers costimulate CD8+ T cells and inhibit tumor growth in mice. J Clin Invest, 2008, pp. 376-386, vol. 118.
Tang et al, Selection of Aptamers for Molecular Recognition and Characterization of Cancer Cells. Anal Chem, 2007, pp. 4900-4907, vol. 79.
Ohuchi et al, Selection of RNA aptamers against recombinant transforming growth factor-β type III receptor displayed on cell surface. Biochimie, 2006, pp. 897-904, vol. 88.
Keefe et al, SELEX with modified nucleotides. Curr Opin Chem Biol, 2008, pp. 448-456, vol. 12.
Chen et al, Many NK cell receptors activate ERK2 and JNK1 to trigger microtubule organizing center and granule polarization and cytotoxicity. Proc Natl Acad Sci USA, 2007, pp. 6329-6334, vol. 104.
Li et al, JNK MAP kinase activation is required for MTOC and granule polarization in NKG2D-mediated NK cell cytotoxicity. Proc Natl Acad Sci USA, 2008, pp. 3017-3022, vol. 105.
Barber et al, LFA-1 Contributes an Early Signal for NK Cell Cytotoxicity. J Immunol, 2004, pp. 3653-3659, vol. 173.
Packard et al, Granzyme B Activity in Target Cells Detects Attack by Cytotoxic Lymphocytes. J Immunol, 2007, pp. 3812-3820, vol. 179.
Park et al, Programmable DNA Self-Assemblies for Nanoscale Organization of Ligands and Proteins. Nano Lett, 2005, pp. 729-733, vol. 5.
Radcliff et al, Quantification of effector/target conjugation involving natural killer (NK) or lymphokine activated killer (LAK) cells by two-color flow cytometry. J Immunol Meth, 1991, pp. 281-292, vol. 139.
Tonn et al, Cellular Immunotherapy of Malignancies Using the Clonal Natural Killer Cell Line NK-92. J Hematother Stem Cell Res, 2001, pp. 535-544, vol. 10.
Papa et al, Functional NK assays using flow cytometry. Methods Cell Biol, 1994, pp. 193-207, vol. 42.
Ferrini et al, Bispecific monoclonal antibodies directed to CD16 and to a tumor-associated antigen induce target-cell lysis by resting NK cells and by a subset of NK clones. Int J Cancer, 1991, pp. 227-233, vol. 48.
ISR for PCT/US2009/059432, mailed Jan. 19, 2010.

*Primary Examiner* — Amy Bowman
(74) *Attorney, Agent, or Firm* — McDonnell Boehnen Hulbert & Berghoff LLP

(57) ABSTRACT

The present invention provides a ligand-nucleic acid nanostructure that promotes cell-cell interaction. Specially, the invention provides a ligand-nucleic acid nanostructure for treating tumor in a mammal. The methods of using and making the composition comprising a ligand-nucleic acid nanostructure are also provided.

11 Claims, 17 Drawing Sheets

DNA NANOSTRUCTURES THAT PROMOTE CELL-CELL INTERACTION AND USE THEREOF

CROSS REFERENCE

This application claims the benefit of priority to U.S. provisional application Ser. No. 61/102,702, filed on Oct. 3, 2008, and 61/117,418, filed on Nov. 24, 2008. The disclosures of these applications are herein incorporated by reference in their entireties.

FIELD OF THE INVENTION

The present invention relates to the fields of cell biology, tumor immunology, nucleic acid-based tiling arrays, nanotechnology, and related fields.

BACKGROUND OF THE INVENTION

Cell-cell interactions are important in the development and activities of multi-cellular organisms. Stable cell-cell interactions maintain the integrity and functions of cells in tissues. More transient cell-cell interactions through multivalent ligand-receptor interaction on the cell surface underlie many aspects of immune responses, including target recognition, immune cell activation and target elimination. For example, cells of the immune systems detect foreign antigens presented on the surface of infected cells, or identify and eliminate cancer cells that exhibit aberrant cell surface proteins.

Despite decades of research efforts, cancer remains today's most pressing health concerns. Cancer treatment using small molecules had shown early promises. However, identification of small molecules with anti-cancer activities involves time-consuming and expensive screening processes. Additionally, anti-tumor small molecules often possess debilitating side effects.

Cancer originates from genetic abnormalities that cause the affected cells to behave differently at the molecular level. The molecular alterations of tumor cells can be detected, and subsequently the tumor cells can be rejected by the body's immune surveillance system. Both CD4 helper T cells and CD8 cytotoxic T cells play a pivotal role in tumor immunity. Traditionally, T cell tumor immunity has been ascribed to CD8 cytotoxic T cell. However, it has become increasingly clear that CD4 helper T cells also play a central role in tumor immunity. For example, evidence has shown that CD4 null mice were unable to mount an effective immune response to a certain form of melanoma. (Hung, K et al., 1998. The central role of CD4 T cells in the antitumor immune response. *J. Exp. Med.* 188, pp. 2357-2368). Additionally, both Th0 and Th1 cells have been shown to increase the activity of tumor-specific CTL clones. (Lee, K Y, et al. Immunoregulatory effects of CD4+ T helper subsets in human melanoma. Surgery 1995, 117, pp. 365-72)

CD8 T cells and natural killer (NK) cells are traditionally known as the major players in tumor immunity. The engagement of MHC class I on an antigen presenting cell (APC) with the T cell receptor (TCR) activates CD8 T cells. The activated CD8 cytotoxic T cell can directly kill the tumor cell through well characterized mechanisms. (Abbas, A. K, and Lichtman, 2005. A. H. Cellular and Molecular Immunology. Elsevier Saunders, Philadelphia, Pa.). Tumor cells often contain genetic alterations that result in reduced levels of MHC I expression to evade immune surveillance. The NK cells detect cells with reduced levels of MHC I expression and are activated by the tumor cells with altered levels of surface MHC class I. Activated NK cells release granule contents that induce apoptosis of the target tumor cells.

The anti-tumor effects of T cells are triggered by the interaction and engagement of T cells with the target tumor cells. Attempts have been made to augment tumor immunity by using bi-specific hybrid antibodies that direct immune cells to the proximity of tumor cells (Carter, P. 2001, Bispecific human IgG by design. *J. Immunological Methods.* 248, pp. 7-15). However, the creation of such hybrid antibodies is predicated on the availability of existing antibodies that recognize tumor cells and antibodies that recognize T cells. The knowledge of a wide variety of tumor antigens representative of different types of cancer is also required. Further, the creation and application of bi-specific antibodies faces multiple technical challenges, such as mis-pairing between immunoglobulin H- and L-chains, instability of engineered molecules, difficulty in large scale production, and potential health risk due to the intrinsic immunogenicity of antibodies. The current method is therefore poorly suited for an effective tumor immune therapy with general applicability because it is labor-intensive, unpredictable, time consuming, and costly. Thus, a better designed technology that provides a rapid, robust, and inexpensive approach for augmenting tumor immunity by promoting cell-cell interaction is needed.

SUMMARY OF THE INVENTION

In one aspect, the present invention provides compositions comprising a first ligand that is capable of binding to a receptor of a first cell type, a second ligand that is capable of binding to a receptor of a second cell type, wherein the first ligand and the second ligand are bound to a nucleic acid nanostructure. In one embodiment, the distance between the first ligand and the second ligand on the nucleic acid-nanostructure is about 15-20 nm.

In a preferred embodiment, the first and/or second ligands are aptamers. In certain preferred embodiments, the first aptamer comprises a dimer, trimer, tetramer, or pentamer of an aptamer that is capable of binding to a receptor of the first cell type. In preferred embodiments of any of the above embodiments, the second aptamer comprises a dimer, trimer, tetramer, or pentamer of an aptamer that is capable of binding to a receptor of the second cell type.

In yet another preferred embodiment, the first aptamer comprises a plurality of first aptamers, and the second aptamer comprises a plurality of second aptamers, and the distance between each aptamer in the plurality of first aptamers on the nucleic acid nanostructure is from about 2 nm to about 5 nm and the distance between each aptamer in the plurality of second aptamers on the nucleic acid nanostructure is from about 2 nm to about 5 nm.

In certain preferred embodiments, the nucleic acid nanostructure comprises a nucleic acid tile or a nucleic acid tiling array. In other embodiments, the nucleic acid nanostructure is between 10 nm and 100 nm in length.

In certain preferred embodiments, the first aptamer and the second aptamer are present on the nucleic acid nanostructure at a density of 4-9 aptamers per aptamer-nucleic acid nanostructure; in various other embodiments, at a density of 4-8, 4-7, or 4-6 aptamers per aptamer-nucleic acid nanostructure.

In certain preferred embodiments, the receptors are cell surface receptors. Any receptors suitable for a given use can be used in the present invention, so long as the first cell type and the second cell type are different cell types, including without limitation, T cell receptors (TCR), co-stimulators or activation molecules on effector cells (such as T cells and natural killer (NK) cells), tumor antigens, major histocompatibility complexes (MHC), and other surface molecules or receptors unique to tumor cells. In particular preferred embodiments, the first aptamer is capable of binding to a T cell receptor (TCR), and the second aptamer is capable of binding to a tumor antigen on the cell surface of a target tumor cell. In other preferred embodiments, the first aptamer is capable of binding to a natural killer (NK) cell receptor, and the second aptamer is capable of binding to a tumor antigen on the cell surface of a target tumor cell.

In another aspect, the invention provides compositions comprising a ligand-nucleic acid nanostructure according to any embodiment of the invention and further comprising a pharmaceutically acceptable carrier. In yet another preferred embodiment, the composition further comprises NK cells bound to the first ligand. In a preferred embodiment, the first ligand comprises an aptamer.

In yet another aspect, the present invention provides methods of promoting interactions between a first cell type and a second cell type comprising contacting the first cell type and the second cell type with a composition comprising a first ligand that is capable of binding to a receptor of the first cell type, a second ligand that is capable of binding to a receptor of the second cell type, wherein the first ligand and the second ligand are bound to a nucleic acid nanostructure, and wherein the binding of the first ligand to the first cell type and the binding of the second ligand to the second cell type promotes interactions between the first and the second cell types. In certain preferred embodiments, the method comprising contacting the first cell type and the second cell type with the inventive composition as described herein. In a preferred embodiment, the first and/or second ligands are aptamers.

In certain preferred embodiments, the first cell type is an immune cell, including without limitation a cytotoxic T cell, a helper T cell, and an NK cell, and the second cell type is an altered or damaged cell including without limitation a tumor cell, a hyper-reactive immune cell, and a pathogen-infected cell.

In another aspect, the present invention provides methods for treating a tumor in a mammal comprising administering to a mammal in need thereof an amount effective to treat the tumor of a composition comprising a first ligand that is capable of binding to a receptor on an immune cell, and a second ligand that is capable of binding to a receptor on a target tumor cell, wherein the first ligand and the second ligand are bound to a nucleic acid nanostructure.

In a preferred embodiment, the first and/or second ligands are aptamers. In certain preferred embodiments, the immune cell includes without limitation a CD4 T cell, a CD8 T cell, and an NK cell; in other embodiments, the immune cell is an NK cell. In other preferred embodiments, the tumor cells include without limitation cells derived from various organ or tissues, such as liver, lung, breast, intestine, colon, prostate and hematopoietic cells, as well as brain tissues.

In another aspect, the present invention provides methods of making a composition of the present invention, the method comprising combining a first ligand, a second ligand, and at least one polynucleotide under conditions suitable for hybridization of the first and second ligands to the polynucleotide to form an ligand-nucleic acid nanostructure, wherein the first ligand is capable of binding to a receptor on a first cell type and the second ligand is capable of binding to a receptor on a second cell type. In a preferred embodiment, the first and/or second ligands are aptamers. In certain preferred embodiments, the polynucleotide is part of a nucleic acid tile. In other embodiments, a plurality of polynucleotides are provided to form one or more nucleic acid tiles, wherein the multiple nucleic acid tiles can form at least one nucleic acid tiling array.

In a further aspect, the invention provides methods of making a random multimeric aptamer library comprising combining at least two monomeric aptamers with at least one linker polynucleotide under conditions suitable for specific hybridization of the monomeric aptamers to the linker polynucleotide, wherein each of the monomeric aptamers comprises a first portion of a randomized sequence and a second portion of a predetermined sequence that is complementary to at least a portion of the sequence of the linker polynucleotide.

Specific embodiments of the present invention will become evident from the following more detailed description of certain preferred embodiments and the claims.

DETAILED DESCRIPTION OF THE INVENTION

Figure 1:
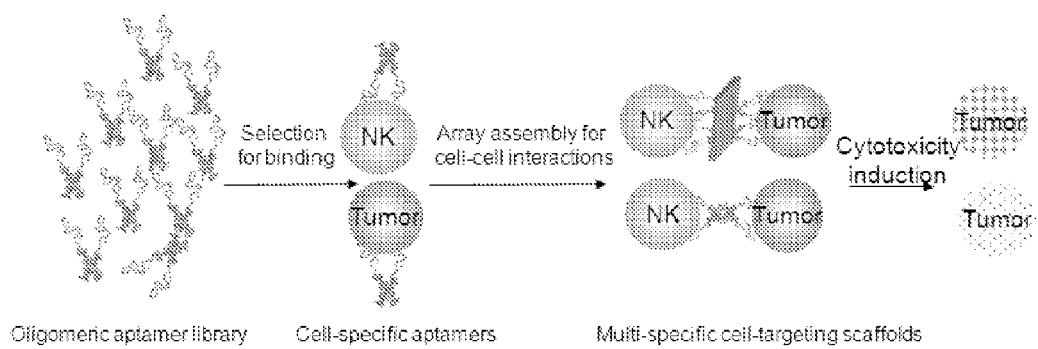
FIG. 1 illustrates an outline of programmable nucleic acid-nanostructure for selection of target-specific multimeric aptamers to direct immune cells (NK cells) to attack tumor cells. The outline depicts a two-step process: 1) selection for aptamers that bind to a target cell; 2) selection for aptamer-nucleic acid nanostructures that bind to and bridge two types of cells.
Figure 2:
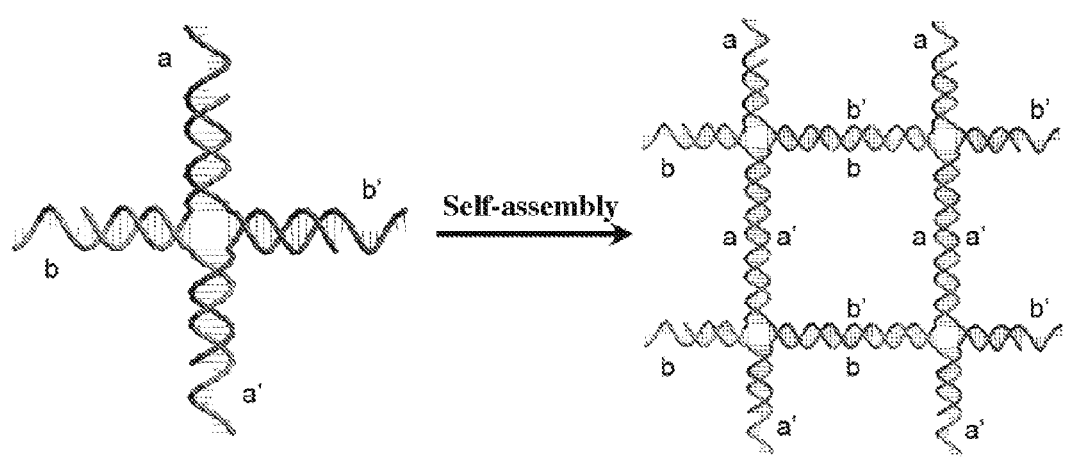
FIG. 2 illustrates DNA tile based self-assembly: combining branched DNA junction with sticky-end associations (e.g. a pairs with a' and b pairs with b') to self-assembled 2D lattices.
Figure 3:
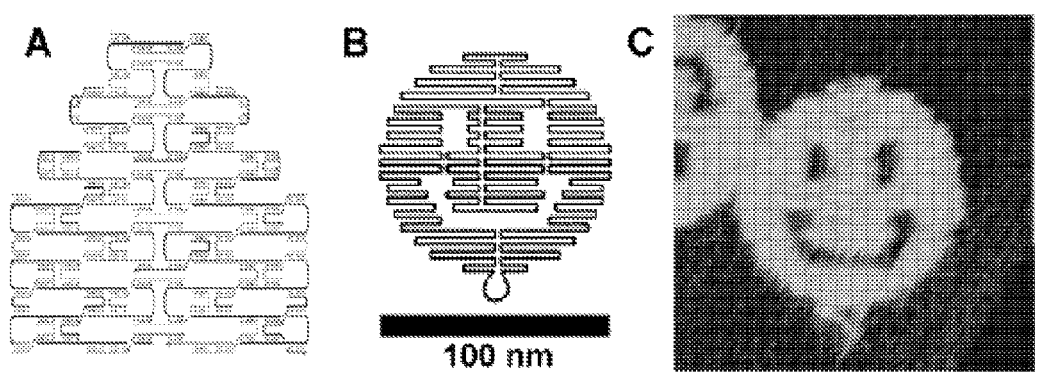
FIG. 3 shows addressable DNA origami arrays self-assembled by folding M13 genomic DNA by short oligonucleotides called helper strands. A) A schematic illustration of the origami design principle. B) The folding pathway of M13 genomic DNA for a single molecule smiley face. C) An AFM image of DNA origami arrays as designed in B.
Figure 4:
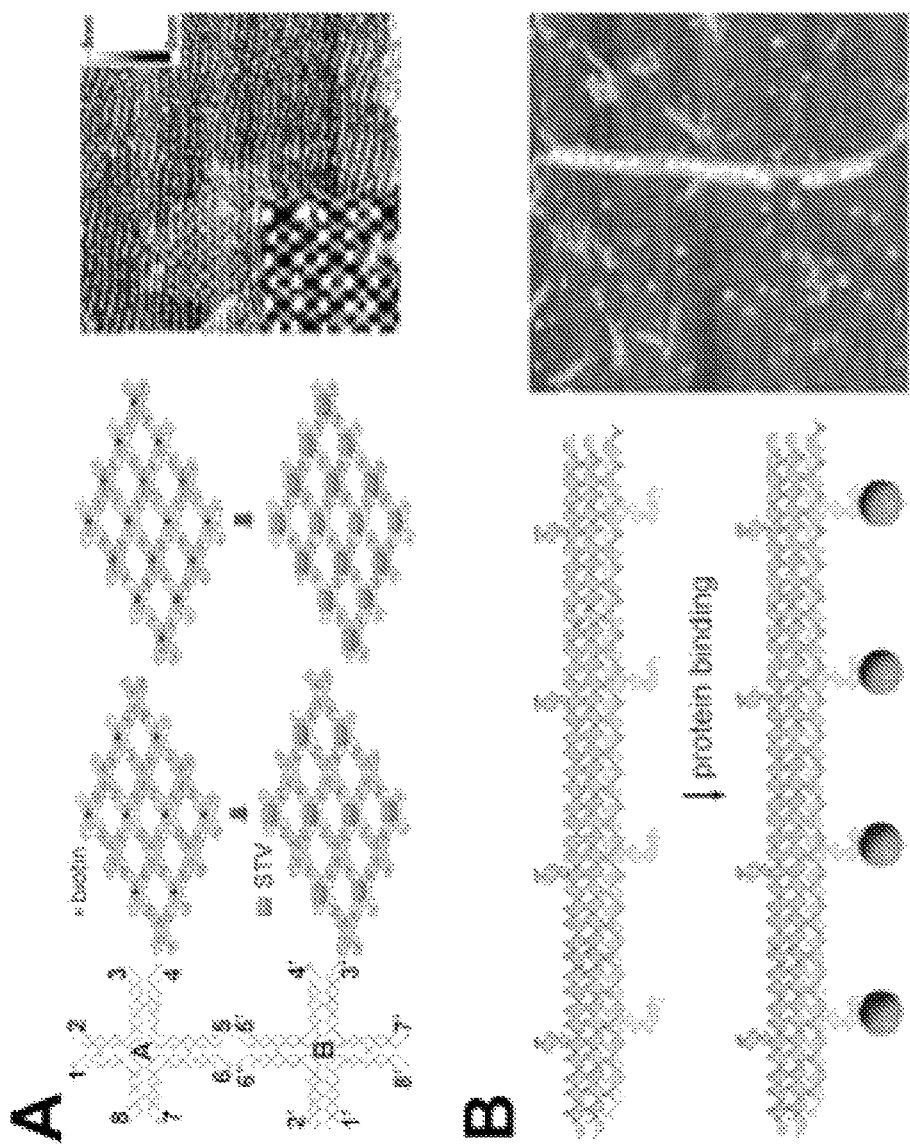
FIG. 4 shows examples of organizing proteins and nanoparticles by DNA-directed self-assembly. A) Schematic diagrams and an AFM (atomic force microscopy) image of the programmed self-assembly of streptavidin on 2D DNA nanogrid. The AFM image is 1000 $nm^2$. B) Schematic diagrams and an AFM image of the aptamer-directed self-assembly of thrombin arrays on DNA templates. The AFM image is 500 $nm^2$. C) Lipoic acid modified DNA provided a bidentate linkage between DNA and Au-NP. When 1:1 conjugates of Au-NP: DNA were mixed with the other DNA strands, DNA tiles carrying discrete number of nanoparticles were obtained with a high yield. D) Process of DNA-tile-directed self-assembly of QD arrays through biotin-streptavidin interaction and TEM image of the periodic pattern of the organized QD arrays.
Figure 4:
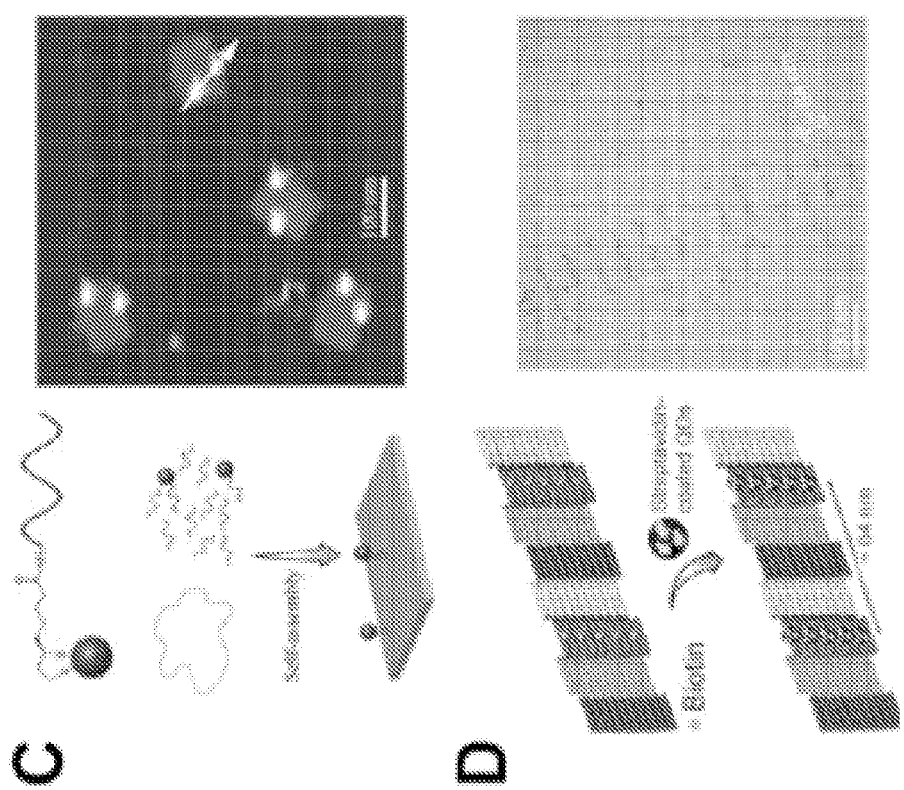

All publications, patents and patent applications cited herein are hereby expressly incorporated by reference for all purposes.

Within this application, unless otherwise stated, the techniques utilized may be found in any of several well-known references such as: *Molecular Cloning: A Laboratory Manual* (Sambrook, et al., 1989, Cold Spring Harbor Laboratory Press) and PCR *Protocols: A Guide to Methods and Applications* (Innis, et al. 1990. Academic Press, San Diego, Calif.).

As used herein, the singular forms "a", "an" and "the" include plural referents unless the context clearly dictates otherwise. For example, reference to a "nucleic acid" means one or more nucleic acids.

As used herein, the terms "polynucleotide", "nucleotide", "oligonucleotide", and "nucleic acid" may be used interchangeably to refer to nucleic acid comprising DNA, RNA, derivative thereof, or combination thereof.

As used herein, the term "binding to" or "bound to" refers to any of direct binding, indirect binding, covalent binding, or non-covalent binding, unless otherwise specifically indicated.

In a first aspect, the invention provides a composition comprising a first ligand that is capable of binding to a receptor of a first cell type, a second ligand that is capable of binding to a receptor of a second cell type, wherein the first and second ligands are bound to the nucleic acid nanostructure. All embodiments in this aspect of the invention apply to all other aspects of the invention.

As used herein the phrases "capable of binding" to a receptor or target molecule and "specific for binding" to a receptor or a target molecule are interchangeable. These terms are used consistently with the terms used in the art of immunology and ligand/receptor interaction in general. For example, an aptamer capable of binding, or specific for binding, to a receptor on a target cell indicates that the aptamer specifically binds to a receptor on a target cell under stringent binding conditions as described herein and that the aptamer's binding under the same binding conditions, if any, to other non-target cell that do not have the same receptor is insubstantial or undetectable as determined by methods commonly used in the immunology or ligand/receptor art. Specific binding can also be determined by competition; for example, a specific binding between a labeled ligand and its receptor under stringent binding conditions can be competed by the unlabeled ligand, but not by other unlabeled irrelevant molecules.

As used herein, the term "ligand" is any molecule capable of binding to a target. Such ligands include, but are not limited to, proteins, lipids, carbohydrates, nucleic acids (including, but not limited to, aptamers), and other molecules. In certain preferred embodiments, the ligand refers to a binding partner that binds to a cell surface receptor. In certain embodiments of the invention, the ligand is a monovalent ligand; in other embodiments, the ligand is a multivalent ligand, which can be without limitation a homomultimeric or heteromultimeric ligand. In certain preferred embodiments, the ligands present on the nucleic acid nanostructure can bind to receptors on the same cell or different cells. In certain preferred embodiments of this aspect, the first ligand comprises the Fc portion of an antibody, and the second ligand comprises an aptamer. In certain preferred embodiments, the first antibody ligand can be non-covalently linked to the second ligand/aptamer by antigen-antibody interaction. In other preferred embodiments, the first ligand comprises a ligand that is capable of binding to an NK cell receptor. In certain other preferred embodiments, the first ligand comprises a ligand that is capable of binding to a CD8 or CD4 T cell receptor. In certain preferred embodiments, the ligand is an aptamer.

In further embodiments, the composition comprises a first aptamer that is capable of binding to a receptor of a first cell type, a second aptamer that is capable of binding to a receptor of a second (different) cell type, wherein the first and second aptamers are bound to the nucleic acid nanostructure. In particular preferred embodiments, the receptor of the first cell type and the receptor of the second cell type are cell surface molecules or receptors. Embodiments of the ligands in various aspects of the invention are often discussed in terms of aptamers; such embodiments will apply to other ligand types disclosed herein, unless the context clearly indicates otherwise.

Cell surface molecules suitable as targets for aptamer binding in the present invention include without limitation, a T cell receptor (TCR), a tumor antigen, a major histocompatibility complex (MHC), and a natural killer (NK) cell surface molecule or receptor. In particular preferred embodiments of this aspect, the first aptamer is capable of binding to a T cell receptor (TCR), and the second aptamer is capable of binding to a tumor antigen on the cell surface of a target tumor cell. In other preferred embodiments, the first aptamer is capable of binding to a natural killer (NK) cell receptor, and the second aptamer is capable of binding to a tumor antigen on the cell surface of a target tumor cell. In various other preferred embodiments, the first aptamer is capable of binding to a TCR or an NK cell receptor, and the second aptamer is capable of binding to an MHC molecule on the surface of a cell infected by a pathogen.

The term "aptamer" as used herein refers to single-stranded nucleic acid molecules with secondary structure(s) that allow binding to a target molecule. In certain preferred embodiments, the single-stranded nucleic acid is ssDNA, ssRNA or derivatives thereof. The aptamer comprises nucleic acid sequence that does not participate in base-pairing with other polynucleotides within the nucleic acid nanostructure.

Aptamers can be synthesized and screened by any suitable methods in the art. For example, aptamers can be screened and identified from a random aptamer library by SELEX (systematic evolution of ligands by exponential enrichment). In certain embodiments, aptamers that bind to a cell surface target molecule can be suitably screened and selected by a modified selection method herein referred to as cell-SELEX or cellular-SELEX as described in Example 3, even if the identity of the cell surface target molecule is unknown. In certain preferred embodiments, a suitable nucleotide length for an aptamer ranges from about 25 to 100 nucleotide (nt), and in various other preferred embodiments, 30-100 nt, 30-60 nt, 25-70 nt, 25-60 nt, 40-60 nt, or 40-70 nt in length. In certain preferred embodiments, the length of an aptamer is about 2-20 nm, in various other preferred embodiments, 2-15 nm, 5-15 nm, 5-10 nm, or less than 10 nm in size. In certain preferred embodiments, the monomeric aptamer contains a predetermined sequence that is about 8-10 nm in length (25-30 nt in length). However, the sequence can be designed with sufficient flexibility such that it can accommodate interactions of aptamers with two targets at the distances described herein.

The flexibility of the monomeric aptamer on the nucleic acid nanostructure or between each monomeric binding units of a multimeric aptamer can be monitored by inserting various length of single stranded-A or T linker oligonucleotide. In certain preferred embodiments, the single stranded-A or T linker oligonucleotide contains 3-10 nucleotides; in certain other preferred embodiments, the single stranded-A/T linker oligonucleotide contains 3-5 nucleotides. In certain preferred embodiments, the single stranded-A/T linker oligonucleotide contains 5-10 nucleotides. It is understood by one of ordinary skill in the art that longer A/T oligonucleotide provides more flexibility.

In certain preferred embodiments of this aspect of the invention, the aptamers comprises multimeric first and/or second aptamers. As used herein, the term "multimeric aptamer" refers to a multimer of aptamers of the same type or different types. The multimer of aptamers can be covalently linked to each other. Alternatively, the multimer of aptamers can be linked to each other by direct base pairing with each other or with a linker polynucleotide, or other non-covalent linkage including without limitation, biotin-streptavidin interaction. Multimeric aptamers provides multivalent binding capacity either for one type of target molecule or receptor, or for multiple types of target molecules or receptors. Multivalent aptamers that bind to multiple types of target molecules are referred to as bi-specific or multi-specific multivalent aptamers. In certain preferred embodiments of this aspect, the first aptamer comprises a dimer, trimer, tetramer, or pentamer of an aptamer that is capable of binding to a receptor of the first cell type, and/or the second aptamers comprises a dimer, trimer, tetramer, or pentamer of an aptamer that is capable of binding to a receptor of the second cell type.

In certain preferred embodiments, the linker polynucleotide has a length between about 5 nucleotides (nt) and about 100 nt; in various other embodiments, 10-30 nt, 20-30 nt, 25-35 nt, 30-50 nt, 40-50 nt, 50-60 nt, 55-65 nt, 50-80 nt, or 80-100 nt. It is within the ability of one of skill in the art to adjust the length of the linker polynucleotide to accommodate each monomeric ligand present on the nucleic acid nanostructure.

Multivalent ligands are known to have higher binding avidity for the target molecules as compared to their monovalent counterparts. A multivalent ligand can be built from its known monomeric unit. A monomeric aptamer that binds to a desired target molecule can be screened and identified from any suitable methods in the art, such as SELEX. The monomeric unit aptamers can be chemically linked to one another to form dimeric or multimeric aptamers.

Figure 11:
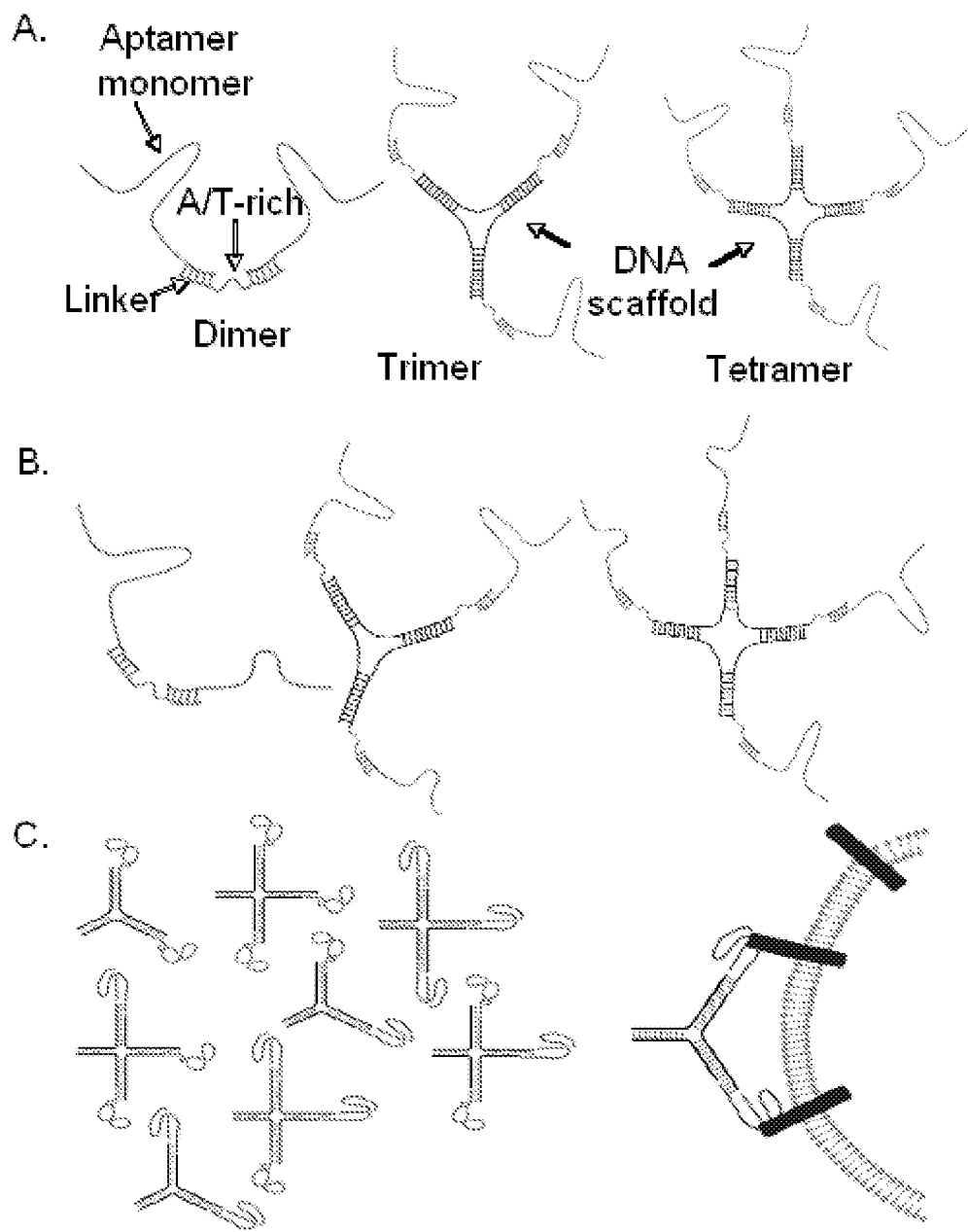
FIG. 11 illustrates representatives of oligomeric aptamer-nanostructures. A) Same aptamer monomer connected by linker polynucleotides to form homomultimers; B) Different aptamers connected by the linker polynucleotides to form heteromultimers; and C) selection of cell-binding aptamers.

In certain preferred embodiments, the multimeric aptamers can be identified and screened from a random multimeric aptamer library as described herein. In other preferred embodiments, the monomeric aptamers are linked to each other by one or a plurality of linker polynucleotides to form multimeric aptamers. Monomeric aptamers can be linked to form multimeric aptamers by any suitable means and in any configurations. Exemplary multimeric aptamers are illustrated in FIG. 11. In certain preferred embodiments, the monomeric aptamer comprises a first portion of a randomized sequence that is about 25 to 100 nucleotides (nt) in length, and in various other preferred embodiments, 30-100 nt, 30-60 nt, 25-70 nt, 25-60 nt, 40-60 nt, or 40-70 nt in length. In certain preferred embodiments, the randomized sequence is 45 nt in length.

In other preferred embodiments, the randomized sequence is flanked by at least one, preferably two, predetermined sequences of about 10-50 nt in length, and in various other preferred embodiments, 15-40 nt, 15-30 nt, 20-40 nt, 25-30 nt, or 20-30 nt in length. In certain preferred embodiments, the predetermined sequence is 20 nt in length. In certain embodiments, each monomeric aptamer nucleic acid comprises a randomized 45 nt sequence flanked by defined 20 nt sequences both upstream and downstream of the random sequence, i.e., the 5'-arm and 3'-arm, respectively. Computer programs are available to assist in designing the suitable predetermined sequence of the 5'-arm and 3'-arm regions to facilitate hybridization with the linker polynucleotide and to minimize potential secondary structure in the 5'-arm and 3'-arm regions. Exemplary computer program includes without limitation Mfold available at web site mobyle.pasteur.fr/cgi-bin/MobylePortal/portal.py?form=mfold.

In certain preferred embodiments of this aspect, randomized dimeric aptamers are formed wherein a linker polynucleotide comprises sequences complementary to both 5'-arm and/or 3'-arm region of random aptamers to form dimeric aptamers. In other preferred embodiments, trimeric or tetrameric aptamers are formed when a plurality of linker polynucleotides that hybridize to the 3'-arm and 5'-arm regions are introduced as illustrated in FIG. 11. In other preferred embodiments, the linker polynucleotide further comprises a single stranded hinge region situated in between the aptamer-binding motifs as illustrated in FIG. 11. In certain preferred embodiments, the hinge region is 3-10 nt in length; in various other embodiments, the hinge region is 3-8 nt, 3-6 nt or 3-5 nt in length. In other embodiments, the hinge region comprises sequence that is rich in As and Ts. The additional single stranded hinge region offers flexibility to allow the multimeric aptamers to coordinate and synergize multivalent interactions with target molecules or receptors.

In certain preferred embodiments, the aptamers are further modified to protect the aptamers from nuclease and other enzymatic activities. The aptamer sequence can be modified by any suitable methods known in the art. For example, phosphorothioate can be incorporated into the backbone, and 5'-modified pyrimidine can be included in 5' end of ssDNA for DNA aptamer. For RNA aptamers, modified nucleotides such as substitutions of the 2'-OH groups of the ribose backbone, e.g., with 2'-deoxy-NTP or 2'-fluoro-NTP, can be incorporated into the RNA molecule using T7 RNA polymerase mutants (Epicentre Biotech, Madison, Wis.). The resistance of these modified aptamers to nuclease can be tested by incubating them with either purified nucleases or nuclease from mouse serum, and the integrity of aptamers can be analyzed by gel electrophoresis.

In certain preferred embodiments of this aspect of the invention, the aptamer, either monomeric or multimeric, can be covalently or non-covalently bound to one or more polynucleotides in the nucleic acid nanostructure; in other preferred embodiments, the aptamer binds to a connector polynucleotide that is directly or indirectly bound to the one or more polynucleotides in the nucleic acid nanostructure. Non-covalent binding includes without limitation nucleic acid base pairing of the aptamer directly with the polynucleotide of the nucleic acid nanostructure (one that remains partially unbound after formation of the nucleic acid nanostructure) or by way of a connector polynucleotide or via biotin-streptavidin interaction.

The integrity of cell binding activities of the aptamers after binding to the nucleic acid nanostructure and/or after being modified to achieve nuclease resistance as described above can be tested by any suitable methods in the art, including without limitation flow cytometry and confocal fluorescent microscopy imaging to ensure that the binding to the nucleic acid nanostructure and/or modification does not compromise the cell binding activity.

In other preferred embodiments of this aspect, the first aptamer comprises a plurality of first aptamers, and/or the second aptamer comprises a plurality of second aptamers, wherein each first aptamer of the plurality of first aptamers and/or each second aptamer of the plurality of second aptamer is a monomeric or multimeric aptamer. Suitable distance between each aptamer of the plurality of first aptamers and between each aptamer of the plurality of second aptamers on the nucleic acid nanostructure is determined by the distance that allows cross-linking of molecules, and coincides with the distance that promotes cooperative binding. The suitable distance can be determined by any suitable methods in the art, including without limitation the method described in Example 1. In certain preferred embodiment, the distance between each aptamer of the plurality of first aptamers and/or each aptamer of the plurality of second aptamers is from about 1 nm to 10 nm; in various other preferred embodiments, between 1 nm and 8 nm; 2 nm and 8 nm; 2 nm and 7 nm; 2 nm and 6 nm, or 2 nm and 5 nm.

The distance between each aptamer of the plurality of aptamers on the nucleic acid nanostructure can be adjusted by changing the length of the aptamer nucleic acid or a connector polynucleotide by which the aptamer is bound to the nucleic acid nanostructure. In certain preferred embodiments, the adjustment of spacing is based on known parameters of B-DNA. For example, it is known that B-DNA is 3.4 angstrom per base pair rise, and 2 nm in diameter. In other embodiments, the spacing can be adjusted by lengthening or shortening the aptamer sequences or the connector sequences. The spacing can be determined and verified by any suitable methods in the art, including without limitation atomic force microscopy (AFM) and Fluorescent Resonant Energy Transfer (FRET).

In certain preferred embodiments, the binding affinity for each aptamer-nucleic acid nanostructure with a defined spatial arrangement of aptamers is determined. In one embodiment, fluorophore-labeled aptamer-nucleic acid nanostructures are incubated with target cells and their binding activity is examined by flow cytometry. The binding affinity is determined by the mean fluorescence intensity of target cells bound with fluorophore-labeled aptamers, as described by Tang et al. (Tang, 2007, Selection of aptamers for molecular recognition and characterization of cancer cells. Anal. Chem. 79:4900) In certain preferred embodiments, the spacing between each aptamers of the same type or different types on the nucleic acid nanostructure can be adjusted to modulate binding affinity of the aptamers to the cell surface receptors.

In certain preferred embodiments, the distance between the first aptamer and the second aptamer on the aptamer-nucleic acid nanostructure is between about 10-50 nm; in various further preferred embodiments, between about 10-40 nm; 10-30 nm; 15-30 nm; 15-25 nm; or 15-20 nm. In certain preferred embodiments, the distance between the first aptamer and the second aptamer on the aptamer-nucleic acid nanostructure is between about 15-20 nm.

In certain preferred embodiments of this aspect, both the first aptamer and the second aptamer are each present on the nucleic acid nanostructure at a density of 2-20 aptamers per nucleic acid nanostructure; in various other preferred embodiments, between 2-15; 2-10; 4-20; 4-15; 4-10; 2-9; 4-9; 4-8; 2-8; 4-6; or 2-6 aptamers per nucleic acid nanostructure. In certain preferred embodiments, the first aptamer is present on the nucleic acid nanostructure at a density of 4-10 aptamers per nucleic acid nanostructure, and the second aptamer is present on the nucleic acid nanostructure at a density of 4-10 aptamers per nucleic acid nanostructure.

In various further preferred embodiments, the composition comprises further ligands (third, fourth, fifth, etc.) as may be suitable for a given intended use. All embodiments of the first and second ligands further apply to further ligands. In certain preferred embodiments, the further ligands are aptamers.

As used herein, the term "nucleic acid nanostructure" or "nanostructure" refers to a nucleic acid structure that includes at least one nanoscale dimension, wherein the nucleic acid structure comprises one or more single stranded nucleic acids, which hybridize to form at least a partially double-stranded structure with defined features and geometry. The nucleic acid nanostructure presents ligands bound thereto to the target cell surface molecules on different cells, and the resulting binding promotes cell-cell interaction. In some preferred embodiments, the nucleic acid nanostructure comprises a double-stranded DNA linker molecule. In certain preferred embodiments, the nucleic acid nanostructure comprises a DNA tile; in certain other preferred embodiments, the nucleic acid nanostructure comprises a DNA tiling array.

Figure 13:
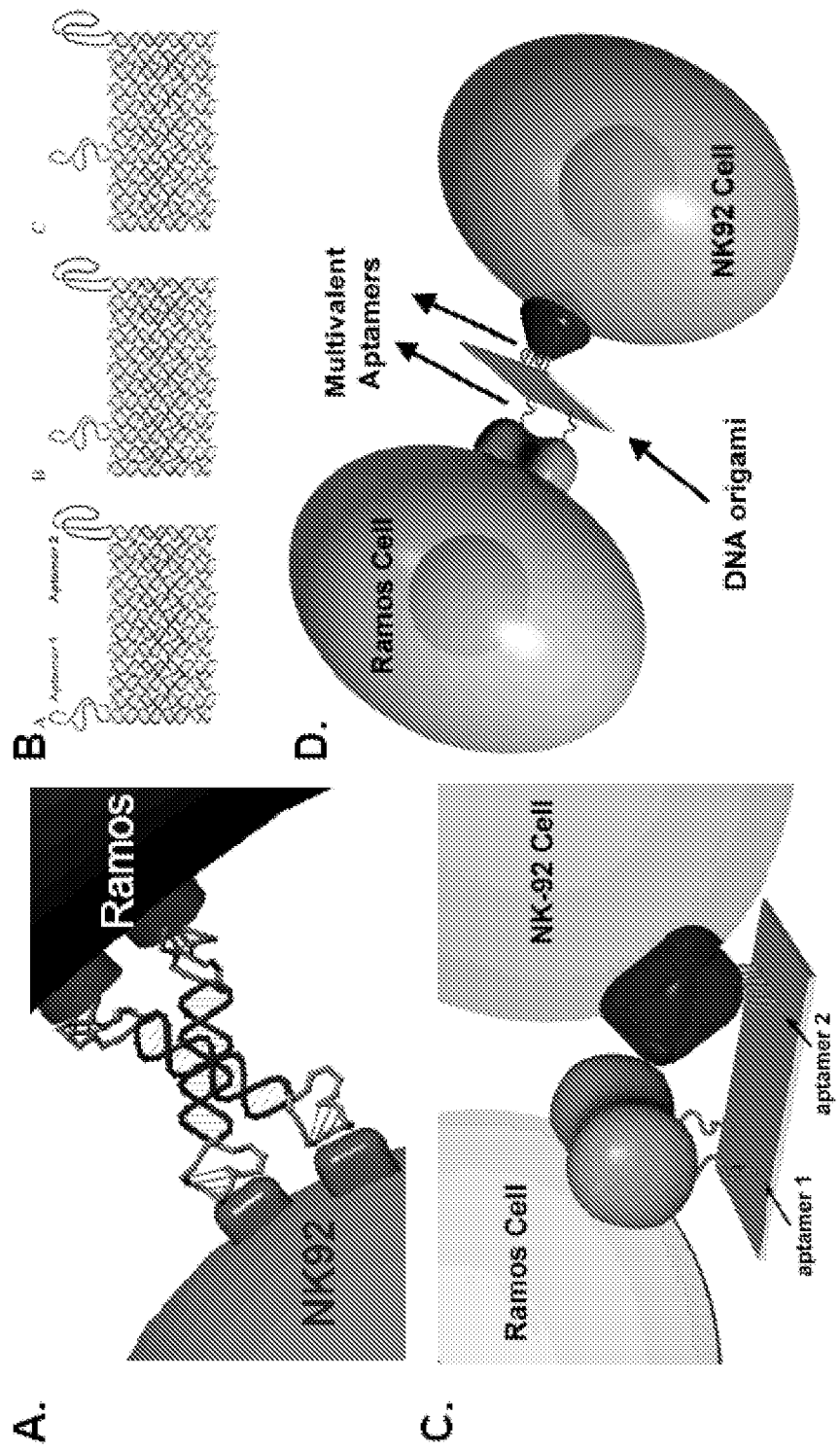
FIG. 13 illustrates representative DNA-nanostructures of aptamer-DNA nanostructures to engage cell-cell interactions. A) Spiral DNA scaffolds. B) DNA origami holding aptamers at different positions. C) and D) Representative configurations of multi-specific DNA origami to direct NK cells to tumor (Ramos) cells.

A variety of suitable nucleic acid nanostructures are known in the art. In certain embodiments, the nucleic acid nanostructure comprises a spiral DNA scaffold, a DNA origami, or a DNA tile or tiling array. Various suitable nucleic acid nanostructures are exemplified in FIG. 13. Such nucleic acid nanostructures are formed by base pairing of single stranded DNA or derivatives thereof or by other non-covalent linkage, such as biotin-streptavidin interaction.

As used herein, "nucleic acid" means DNA, RNA, peptide nucleic acids ("PNA"), and locked nucleic acids ("LNA"), nucleic acid-like structures, as well as combinations thereof and analogues thereof, unless specifically indicated. Nucleic acid analogues include known analogues of natural nucleotides which have similar or improved binding properties. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs), methylphosphonate linkages or alternating methylphosphonate and phosphodiester linkages (Strauss-Soukup (1997) Biochemistry 36:8692-8698), and benzylphosphonate linkages, as discussed in U.S. Pat. No. 6,664,057; see also Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS1992); Milligan (1993) J. Med. Chem. 36:1923-1937; Antisense Research and Applications (1993, CRC Press). In preferred embodiments, the nucleic acid nanostructure comprises a DNA tile or DNA tiling array.

Synthesis of polynucleotides is well known in the art. See, for example, Yan, H. et al., *Science* 2003, 301, 1882-1884; U.S. Pat. No. 6,255,469; WO 97/41142; Seeman, N. C., Chem Biol, 2003. 10: p. 1151-9; Seeman, N. C. N., 2003. 421: p. 427-431; Winfree, E. et al., Nature, 1998. 394: p. 539-44; Fu, T. J. and N. C. Seeman, Biochemistry, 1993. 32: p. 3211-20; Seeman, N. C., J Theor Biol, 1982. 99: p. 237-47; Storhoff, J. J. and C. A. Mirkin, Chem. Rev., 1999. 99: p. 1849-1862; Yan et al., PNAS 100, Jul. 8, 2003 pp 8103-8108); and WO2006/124089. It is highly desirable, but not essential, in making the polynucleotides for the nucleic acid tiles to appropriately design sequences to minimize undesired base pairing and undesired secondary structure formation. Computer programs for such purposes are well known in the art. (See, for example, Seeman, N. C., J Biomol Struct Dyn, 1990. 8: p. 573-81). It is further preferred that the polynucleotides are purified prior to nucleic acid tile assembly. Purification can be by any appropriate means, such as by gel electrophoretic techniques.

In certain preferred embodiments of this aspect, the nucleic acid nanostructure comprises a multi-helical bundle to display aptamers. The multi-helical bundle comprises 2-20 double stranded helices; in various other preferred embodiments, the multi-helical bundle comprise 2-15, 2-12, 2-10, 3-20, 3-12, 3-10, 4-20, 4-10, 4-8 double stranded helices. It is within the skill of one of ordinary skill in the art to determine the suitable number of double stranded helices suitable for use as nucleic acid nanostructure in the present invention. In certain other preferred embodiments, the nucleic acid nanostructure comprises a rectangular DNA origami carrying two types of multivalent aptamers at the same or opposite side of the planer. In certain preferred embodiments, the nucleic acid nanostructure is 50-200 nm (i.e., 50×50 $nm^2$ to 200×200 $nm^2$); in other embodiments, 10-200 nm; 25-200 nm; 25-100 nm; 50-200 nm; 50-150 nm; or 50-100 nm in length. In certain preferred embodiments, the nucleic acid nanostructure is 100 nm in length (i.e.: 100×100 $nm^2$).

In certain preferred embodiments of the invention, the nucleic acid nanostructure comprises one or more nucleic acid tiles, preferably DNA tiles. Self-assembling nucleic acid tiling lattices represent a versatile system for nanoscale construction. Structure formation using nucleic acid 'smart tiles' begins with the chemical synthesis of single-stranded polynucleotides, which when properly annealed, self-assemble into nucleic acid tile building blocks through Watson-Crick base pairing. DNA tiles bearing complementary sticky ends are then able to further self-assemble into larger arrays with distinct topological and geometric features. A self-assembling, finite nucleic acid-based nanoarray allows a wide variety of discrete molecules to be placed at specific locations with nm-scale accuracy. Various nucleic acid tiles and tiling array have been described in the art. (See for example WO2008/033848 and WO2006/124089, the disclosures of which are incorporated herein by reference in their entirety.)

The dimensions of a given nucleic acid tile can be programmed, based on the length of the polynucleotides of the nucleic acid nanostructure (i.e.: those polynucleotides that are integrally involved in the structure of the nucleic acid tile) and their programmed shape and size, the length of the sticky ends (when used), and other design elements. Based on the teachings provided herein and known in the art, those of skill in the art can prepare nucleic acid tiles of any desired size. In various preferred embodiments the length and width of individual nucleic acid tiles are between 3 nm and 100 nm; in various other preferred embodiments, widths range from 4 nm to 60 nm and lengths range from 10 nm to 90 nm. In certain preferred embodiments, the nucleic acid nanostructure comprises a singe nucleic acid tile or a nucleic acid tiling array that has a dimension consistent with the dimension of a nucleic acid nanostructure as described above suitable for use in the present invention.

In one preferred embodiment, the nucleic acid nanostructure comprises or consists of a nucleic acid tiling array, comprising a plurality of nucleic acid tiles joined to one another via sticky ends, wherein each nucleic acid tile comprises one or more sticky ends, and wherein a sticky end for a given nucleic acid tile is complementary to a single sticky end of another nucleic acid tile in the nucleic acid tiling array; wherein the nucleic acid tiles are present at predetermined positions within the nucleic acid tiling array as a result of programmed base pairing between the sticky ends of the nucleic acid tiles. In this embodiment, one or more tiles in the array comprise nucleic acid probes for binding the ligands to the nanostructure.

As used herein, "programmed base pairing" means that the sticky ends for the different nucleic acid tiles are designed to ensure interactions of specific nucleic acid tiles through their complementary sticky ends, thus programming the position of the nucleic acid tile within the nucleic acid tiling array. As used herein, "predetermined positions" means that the ultimate position of each nucleic acid tile in the self-assembled nucleic acid tiling array is based on the sequence and position of its sticky ends and the sequence and position of the sticky ends of the other nucleic acid tiles in the nucleic acid tiling array, such that the plurality of nucleic acid tiles can only assemble in one specific way.

Since the position of all nucleic acid tiles in the array is predetermined, the boundary tiles are also predetermined, and thus the nucleic acid tiling arrays of the present invention have defined boundaries (ie: "finite" nucleic acid tiling arrays).

Each "nucleic acid tile" comprises (a) a structural element (also referred to herein as the polynucleotide "core") constructed from a plurality of nucleic acid polynucleotides; and (b) 1 or more "sticky ends" per nucleic acid tile attached to the polynucleotide core. Those of skill in the art are well aware of the wide range of such polynucleotide cores, including but not limited to 4 arm branch junctions, 3 arm branch junctions, double crossovers, triple crossovers, parallelograms, 8 helix bundles, 6-tube formations, and structures assembled using one or more long strands of nucleic acid that are folded with the help of smaller 'helper' strands (See, for example, Yan, H. et al., *Science* 2003, 301, 1882-1884; U.S. Pat. No. 6,255,469; WO 97/41142; Seeman, N. C., Chem Biol, 2003. 10: p. 1151-9; Seeman, N. C. N., 2003. 421: p. 427-431; Winfree, E. et al., Nature, 1998. 394: p. 539-44; Fu, T. J. and N. C. Seeman, Biochemistry, 1993. 32: p. 3211-20; Seeman, N. C., J Theor Biol, 1982. 99: p. 237-47; Storhoff, J. J. and C. A. Mirkin, Chem. Rev., 1999. 99: p. 1849-1862; Yan et al., Proceedings of the National Academy of Sciences 100, Jul. 8, 2003 pp 8103-8108.)

Self-assembly of a plurality of nucleic acid tiles results in programmed base-pairing interactions between sticky ends on different nucleic acid tiles to form the nucleic acid tiling arrays.

As used herein, a "plurality" of nucleic acid tiles means 4 or more nucleic acid tiles. In various preferred embodiments, the nucleic acid tiling array contains at least 6, 9, 16, 25, 36, 49, 64, 81, 100, 121, 144, 169, 206, 225, 256, 289, 324, 361, or 400 nucleic acid tiles.

As used herein, a "nucleic acid tiling array" is the assembled array of nucleic acid tiles of the invention based on specific Watson-Crick base pairing between sticky ends of different nucleic acid tiles. Each nucleic acid tile within the nucleic acid tiling array is located at a pre-determined position in the array, based on the complementarity of its "sticky ends" to sticky ends on a different nucleic acid tile. As will be apparent to those of skill in the art, a given nucleic acid tile may specifically bind to only one other nucleic acid tile in the nucleic acid tiling array (if the given nucleic acid tile is programmed with only a single sticky end), or it may interact with 2, 3, 4, 5, 6, 7, 8, 9, 10, 11, 12, or more other nucleic acid tiles in the nucleic acid tiling array if the given nucleic acid tile has 2, 3, 4, 5, 6, 7, 8, 9, 10, 11, 12, or more sticky ends, respectively. For example, closely packed arrays typically utilize 2-12 sticky ends, but more sticky ends might be used in an array that branched from a central point, as in a dendrimeric nucleic acid tiling array.

As discussed above, the nucleic acid tiles in the tiling array include "boundary tiles", nucleic acid tiles that are programmed for self-assembly at the edge of the nucleic acid tiling array based on their sticky end composition. As a result, the nucleic acid tiling array is finite. In a preferred embodiment, one or more boundary tiles in the nucleic acid tiling array further comprise modification of one or more polynucleotides that terminate further self-assembly. In a non-limiting example, the modification comprises addition of "TTT" (or some other sequence that has no complement within the array) overhangs at the parts of each tile that lies at the edge of the array (or adjacent to holes in it) such that the array must not be continued beyond those points. Alternatively, no sticky ends are placed on those sections of the tiles that lie at the edges of the arrays, terminating them instead with blunt-ended nucleic acid, such as double helical DNA (and thus these boundary tiles only have sticky ends to tie into the existing array, but not to extend it).

In a further embodiment, sticky-ends can be added to the edge of the finite size arrays, thus allowing hierarchical assembly of larger arrays with defined dimensions. In this embodiment, sticky ends that are not complementary to any of the stick ends on the nucleic acid tiling array, are added to the edge of the array to permit complementary binding to any other structure of interest, such as a second finite array.

In a further preferred embodiment, the nucleic acid tiling array comprises an indexing feature to orient the tiling array and thus facilitate identification of each individual nucleic acid tile in the array. Any indexing feature can be used, so long as it is located at some spot on the array that has a lower symmetry than the array itself. Examples of such indexing features include, but are not limited to: (1) including one or more tiles that impart(s) an asymmetry to the array; (2) including one or more tiles that is/are differentially distinguishable from the other tiles (for example, by a detectable label); for example, a biotin molecule that could later be marked by exposing the array to streptavidin; (3) including any protrusion on an edge of the array that is offset from two edges by unequal amounts, which will serve to index the array even if it is imaged upside down; (4) including a high point on the array that is detectable; (5) introducing one or more gaps in the tiling array that introduce a detectable asymmetry; and (6) making the nucleic acid tiling array of low enough symmetry with respect to rotations and inversions that locations on it could be identified unambiguously; for example, a nucleic acid tiling array in the shape of a letter "L" with unequal sized arms would serve such a purpose.

As used herein, a "sticky end" is a single stranded base sequence attached to the polynucleotide core of a nucleic acid tile. For each sticky end, there is a complementary sticky end on a different nucleic acid tile with which it is designed to bind, via base pairing, within the nucleic acid tiling array. Each nucleic acid tile must contain at least one sticky end (for example, in a boundary nucleic acid tile of certain embodiments), but may contain 2, 3, 4, 5, 6, 7, 8, 9, 10, 11, 12, or more sticky ends, depending on the design of the nucleic acid tiling array.

The sticky ends are incorporated into the nucleic acid tile as a portion of one or more of the core polynucleotides. Such incorporation can be carried out in a variety of ways, in part depending on the type of polynucleotide core used.

The length of the sticky ends for each nucleic acid tile can vary, depending on the desired spacing between nucleic acid tiles, the number of nucleic acid tiles in the nucleic acid tiling array, the desired dimensions of the nucleic acid tiling array, and any other design parameters such as the desired distance between ligands attached to the array. The sticky ends do not have to be of identical length for a given nucleic acid tile or relative to other nucleic acid tiles in the nucleic acid tiling array, so long as a complementary sticky end of an identical length is present on the nucleic acid tile to which it is designed to base pair. Alternatively, the sticky ends on all of the nucleic acid tiles can be of identical length. Particularly preferred lengths of the sticky ends are 4, 5, 6, 7, 8, 9, or 10 nucleotides.

In one preferred embodiment, each sticky end for a given nucleic acid tile is (a) different than the other sticky ends for that nucleic acid tile; (b) unique to that nucleic acid tile with respect to all other nucleic acid tiles in the array; and (c) complementary to a single sticky end of one other nucleic acid tile in the nucleic acid tiling array. As will be apparent to those of skill in the art, the polynucleotide structural element of each nucleic acid tile can be identical in this embodiment, so long as the sticky ends are unique. Thus, in this embodiment, a nucleic acid tiling array with "N" tiles is made by synthesizing "N" different tiles, each containing unique sticky-ends to connect to its neighboring tiles, so that each tile takes up a unique and well defined position in the array.

In a preferred embodiment, the nucleic acid tiles are not all unique (i.e.: some of the nucleic acid tiles may contain the same sticky ends). The nucleic acid tiling strategy in this embodiment takes advantage of the geometric symmetry of the nucleic acid tiling array. In general, to use a total of N tiles to construct a fixed size 2D nucleic acid tiling array with $C_m$ symmetry, where m=2, 3, 4, or 6, the number of unique tiles the fixed size array requires is N/m, if N/m is an integral number, or Int (N/m)+1, if N/m is an non-integral number. This strategy is cost-effective in material, particularly when combined with embodiments where the polynucleotide structural element for each nucleic acid tile is identical. This embodiment minimizes polynucleotide design time and the sample preparation time dramatically. In these embodiments, the total number of unique sticky end pairs is preferably $N*(N-1)/2$.

In a preferred embodiment of each of the above embodiments, each nucleic acid tile comprises an identical polynucleotide structural element, which limits the number of different polynucleotides that must be synthesized and assembled. In this embodiment, the nucleic acid tiles differ in their sticky ends, which program the predetermined position of each nucleic acid tile in the nucleic acid tiling array. As disclosed below, the nucleic acid tiles in this and all other embodiments may contain further components in addition to the polynucleotide structural element and the sticky ends, and these further components may differ between different nucleic acid tiles.

In a preferred embodiment, the resulting nucleic acid tiling array is "non-periodic," meaning that the array does not include simple repetitive nucleic acid tile "patterns," such as ABABAB; ABCDABCD; ABABDCDCABABDCDC. This does not require that all of the tiles in the array be unique.

The dimensions of nucleic acid tiling arrays can also be preferably programmed with the use of boundary tiles (i.e., tiles designed to terminate further assembly of the array), depending on the size of the individual nucleic acid tiles, the number of nucleic acid tiles, the length of the sticky ends (when used), the desired spacing between individual nucleic acid tiles, and other design elements. In embodiments that do not incorporate boundary tiles, the size of the arrays depends on the purity of the DNA strands, the stoichiometry of the different polynucleotides, and the kinetics (how slow the annealing process is). Based on the teachings herein and known in the art, those of skill in the art can prepare nucleic acid tiling arrays of any desired size, preferably within a size limit that does not induce internalization of the tiling array by way of phagocytosis of the cell. In certain embodiments, the nucleic acid tile or tiling array is not more than 100 nm in length (i.e.: $100 \times 100$ nm$^2$).

In another preferred embodiment, the nucleic acid nanostructure comprises or consists of a nucleic acid thread strand-based tile, comprises: (a) a nucleic acid thread strand; (b) a plurality of helper nucleic acid strands that are complementary to parts of the nucleic acid thread strand; wherein a plurality of the helper nucleic acid strands further comprises a nucleic acid probe; and wherein the nucleic acid thread strand is folded into a desired shape by hybridization to the helper strands; wherein the nucleic acid thread strand is not complementary to any of the nucleic acid probes, and wherein the predetermined size of the array is determined by the length and shape of the nucleic acid thread strand as folded by helper strands.

As used herein, "the nucleic acid thread strand is not complementary to any of the nucleic acid probes" means that the nucleic acid probes do not base pair with the thread strand over the length of the nucleic acid probe under the conditions used, and thus the helper strands are available for interactions with a target. In this embodiment, no sticky ends are required for self-assembly.

The nucleic acid thread strand can be any suitable polynucleotide of appropriate length and sequence for the desired nucleic acid tile. In one embodiment, the nucleic acid thread strand is a genomic nucleic acid strand, or suitable fragments thereof, such as from a virus, bacterium, or indeed any organism from which long DNA can be extracted. The only caveat is that the chosen section of genomic nucleic acid should not have sequences that are complementary to the probe sequences, and they should not contain significant amounts of repeated sequences or other sequences that might form structures that interfere with assembly of the array (such the G-rich regions that might form quadruplexes as in telomere DNA).

In a preferred embodiment, genomic nucleic acid, or fragments thereof, is used as the nucleic acid thread for lengths above about 50 bp where synthetic nucleic acid becomes expensive and difficult to make. Lengths up to the full length of an organism's genome (ca. $10^9$ bp) are feasible if they met the sequence criteria described above.

The nucleic acid helper strands are complementary to regions of the nucleic acid thread and not to each other, and are designed to hybridize to the nucleic acid thread strand so as to constrain the nucleic acid thread strand into a desired shape. A plurality of the nucleic acid helper strands comprises nucleic acid probes. In one embodiment, helper strands are between 10 and 50 nucleotides, not including any DNA probe that is part of the helper strand.

In a further embodiment, the nucleic acid thread-based tile further comprises nucleic acid filler strands that hybridize to the nucleic acid thread strand. These strands are not involved in shaping the nucleic acid thread strand, but add further structural integrity to the resulting nucleic acid tile. It is further preferred that a plurality of the nucleic acid filler strands further comprises a nucleic acid probe.

In another embodiment, one or more of the helper strands can be part of a larger nucleic acid structure. In one example, one or more helper strands protrude from one or more nucleic acid tiles. The helper strands fold the thread strand into place, and the nucleic acid tiles (and their nucleic acid probes) comprising the helper strands are thus precisely positioned on the thread strand.

In another embodiment, one or more of the helper strands may protrude from one or more nucleic acid arrays (formed by combining two or more nucleic acid tiles). In this embodiment, one or more helper strands protrude from one or more tiling arrays and fold the thread strand into place, and the tiling arrays (and the nucleic acid tiles they are composed of, including nucleic acid probes) comprising the helper strands are thus precisely positioned on the thread strand. In this embodiment, it is possible, for example, to provide unlimited hierarchies of nucleic acid tiling arrays.

The dimensions of a given nucleic acid thread strand-based tile can be programmed, based on the available length and sequence of thread strand nucleic acid, and other design elements. For example, a 10,000 base thread strand nucleic acid could be formed into a nucleic acid tile covering an area of approximately 2 nm×10,000×0.3 nm or $6×10^{-15}$ m$^2$. This would correspond to a square of about 0.1 µm on each side. Depending upon the design of the thread strand-based nucleic acid tile, the size of the nucleic acid probe, the specific target, and other design feature, the density of target molecules on the nucleic acid tile can be as high as $10^{12}$ per square cm.

In this most preferred embodiment, the nucleic acid thread-based tile can be assembled in one step. A long template strand of nucleic acid is mixed with shorter 'helper' strands, usually in a large molar excess of the shorter strands. The strand sequences are chosen to fold the long template strand into the desired shape, as described by Yan et al. (Proceedings of the National Academy of Sciences 100, Jul. 8, 2003 pp 8103-8108.) The probe array is then achieved by using one or more helper strands with nucleic acid probes that are not complementary to any part of the template strand or the other helper strands. These will then protrude from the array, forming single stranded probe strands at known locations if the array contains an index feature. General conditions for such hybridization are known in the art.

The rigidity and well-defined geometry of nucleic acid nanostructures provide superb spatial and orientational control of the ligands on the array. The spacing of the ligands and their positioning with respect to, for example, a tiling array surface can be precisely controlled to the sub-nanometer scale. This not only allows optimization of geometry for fast kinetics, it also allows efficient rebinding of the receptor to nearby ligands and leads to improved binding efficiency. The well separated positioning of the ligands on the array also allows efficient binding of different receptors to bind corresponding ligands on the tiling array.

As will be apparent to those of skill in the art, in this embodiment, not all of the nucleic acid tiles in a nucleic acid tiling array are required to possess a ligand. Thus, one or more of the nucleic acid tiles in the nucleic acid tiling array comprises a ligand; preferably a majority of the nucleic acid tiles in the array comprise a ligand; more preferably all of the nucleic acid tiles comprise a ligand.

In certain preferred embodiments, the composition further comprises a pharmaceutically acceptable carrier, excipient or diluent. Suitable carrier, excipient or diluent includes without limitation water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, and oils. Any other suitable pharmaceutically acceptable carrier excipient or diluent that does not disrupt the stability and binding capacity of the aptamer nucleic acid nanostructure can be used in the present invention.

In certain preferred embodiments, the composition further comprises NK cells, preferably NK cells derived from a mammal in need of the composition. In certain embodiments, established NK cell lines of human origin are used. In other embodiments, NK cells isolated from the blood of a mammal in need of the composition are used. Methods of isolating NK cells from the blood of a mammal are known in the art; exemplary methods can be found in Binyamin, et al, 2008, Blocking NK cell inhibitory self-recognition promotes antibody-dependent cellular cytotoxicity in a model of anti-lymphoma therapy. J. Immunol. 180:6392.

In another aspect, the invention provides methods of making a random multimeric aptamer library comprising combining at least two monomeric aptamers with at least one linker polynucleotide under conditions suitable for specific hybridization of the monomeric aptamers to the linker polynucleotide, wherein each of the monomeric aptamer comprises a first portion of a randomized sequence and a second portion of a predetermined sequence that is complementary to at least a portion of the sequence of the linker polynucleotide.

As used herein, the term "randomized sequence" refers to an undefined nucleic acid molecule that contains degenerative nucleotide residues at some or all positions. Nucleic acid containing randomized sequence can be chemically synthesized by various methods known in the art and described herein.

As used herein, the term "predetermined sequence" refers to a defined nucleic acid molecule for which the nucleotide sequence is known. Nucleic acid containing randomized sequence can be chemically synthesized by methods known in the art and described herein or produced recombinantly in a cell.

In certain preferred embodiments, the predetermined sequence is complementary to at least 10 nt of sequence of the linker polynucleotide; in various other preferred embodiments, at least 15 nt, 20 nt, 25 nt, 30 nt, 35 nt, 40 nt, 45 nt or 50 nt of the sequence of the linker polynucleotide.

All embodiments of aptamers, linkers, etc. described herein are applicable to this aspect of the invention as well. All embodiments of this aspect can be applied to any other aspects of the invention.

In yet another aspect, the invention provides methods of making an nucleic acid nanostructure, the method comprising contacting a first aptamer, a second aptamer, and at least one polynucleotide under conditions suitable for binding of the first and second aptamers to the polynucleotide to form an aptamer-DNA nanostructure, wherein the first aptamer is capable of binding to a receptor on a first cell type and the second aptamer is capable of binding to a receptor on a second cell type, and wherein the polynucleotide forms a nucleic acid nanostructure. In certain preferred embodiments, the first and second aptamers directly bind to the polynucleotide, or indirectly through a connector polynucleotide that is bound to the polynucleotide. In various other preferred embodiments, the first and second aptamers bind to the polynucleotide non-covalently by ways of, including without limitation, base pairing and biotin-streptavidin interaction. In certain embodiments of this aspect, the polynucleotide is part of a nucleic acid tile.

In another preferred embodiment, the nucleic acid nanostructure comprises a plurality of polynucleotides, and wherein the contacting is done under conditions suitable to promote hybridization of the plurality of polynucleotides into at least one nucleic acid tile. In yet further preferred embodiments, the plurality of polynucleotides forms a plurality of nucleic acid tiles, and wherein the plurality of nucleic acid tiles forms at least one nucleic acid tiling array.

The particular hybridization buffers and other conditions employed can vary depending on the polynucleotide lengths and sequences, and are well within the level of skill in the art based on the teachings herein. Any suitable hybridization conditions known in the art can be adopted. Exemplary hybridization conditions are provided as follows. The nucleic acid nanostructures carry a considerable negative charge at low salt, and therefore hybridization in the presence of a significant amount of salt (e.g., 10 mM $MgCl_2$ or 600 mM or greater monovalent salt like NaCl) is preferred. Other typical annealing conditions include 1 M NaCl and 10 mM $NaHPO_4$ (pH7). Aptamers (when included as ligands) typically require 10 mM $MgCl_2$ to fold properly. General parameters for hybridization conditions for nucleic acids are described in Sambrook et al., supra, and in Ausubel et al., 1987, Current Protocols in Molecular Biology, Greene Publishing and Wiley-Interscience, New York.

In certain preferred embodiments, the stoichiometric amount of each polynucleotide in a nucleic acid nanostructure is combined under denaturing conditions, such as between 90° C. and 99° C., followed by cooling to between 25° C. and 50° C. in appropriate hybridization buffer, as can be determined by those of skill in the art. In a preferred embodiment, annealing protocols involve a high temperature and low salt denaturing step, followed by a low temperature high salt annealing step. In this embodiment, the high salt concentrations are not added to the reaction until the polynucleotides are removed from the heat and placed on ice.

The polynucleotide concentration used can vary, and those of skill in the art, based on the teachings provided herein and known in the art, can determine appropriate concentrations. In one preferred embodiment, polynucleotide concentration is between 1 nm and 10 μM.

In certain preferred embodiments, the nucleic acid nanostructure comprises a plurality of nucleic acid tiles that are combined under conditions suitable to promote hybridization of the sticky ends between different nucleic acid tiles. In a preferred embodiment, such suitable conditions include incubation in appropriate hybridization solution at a beginning temperature of between 25° C. and 45° C., followed by cooling in the same hybridization buffer to between 5° C. and 25° C. over 1 hour to 24 hours. The specific condition chosen need to balance the needs between avoiding disassembly of the tiles, which generally have melting temperatures in the range of 50-65° C., and to eliminate the possible mismatches among the different sticky ends of the tiles. In a preferred embodiment, the buffer condition used comprises 40 mM Tris, 20 mM acetic acid, 2 mM EDTA, and 12.5 mM magnesium acetate, pH 8.0.

In a preferred embodiment, synthesis of the nucleic acid tiling arrays comprises separating free nucleic acid tiles and/or incompletely hybridized nucleic acid tiles from completely formed nucleic acid tiling arrays. Any appropriate separation method can be used, including but not limited to size exclusion chromatography, sucrose gradient centrifugation, and affinity based separation techniques. In a preferred embodiment, the nucleic acid tiling arrays are chemically modified so as to permit affinity-based separation techniques. Any chemical modification that permits such affinity-based separation techniques can be used, including but not limited to, chemically modifying the nucleic acid tiling array to contain one or more biotin residues, which can then be used for streptavidin-based affinity separation of the nucleic acid tiles.

The compositions of the invention can be made and stored as described herein. In various preferred embodiments, the compositions may be present in solution, or in lyophilized form. All the embodiments of this aspect of methods of making a nucleic acid nanostructure can be used in conjunction with any other aspects of the invention.

In a further aspect, the invention provides a method of promoting cell-cell interaction. In this aspect, a first cell type and a second cell type are allowed to contact with a composition comprising a first aptamer that is capable of binding to a receptor of the first cell type, a second aptamer that is capable of binding to a receptor of the second cell type, wherein the first aptamer and the second aptamer are bound to a nucleic acid nanostructure, and wherein the binding of the first aptamer to the first cell type and the binding of the second aptamer to the second cell type promotes interactions between the first and the second cell types. In certain preferred embodiments, the first cell type is an immune cell, including without limitation a cytotoxic T cell, a helper T cell, and an NK cell, and the second cell type is a target cell, including without limitation a tumor cell, or antigen presenting cell infected by a pathogen. In various preferred embodiments, the pathogen is a bacterium, a virus or a fungus.

Figure 14:
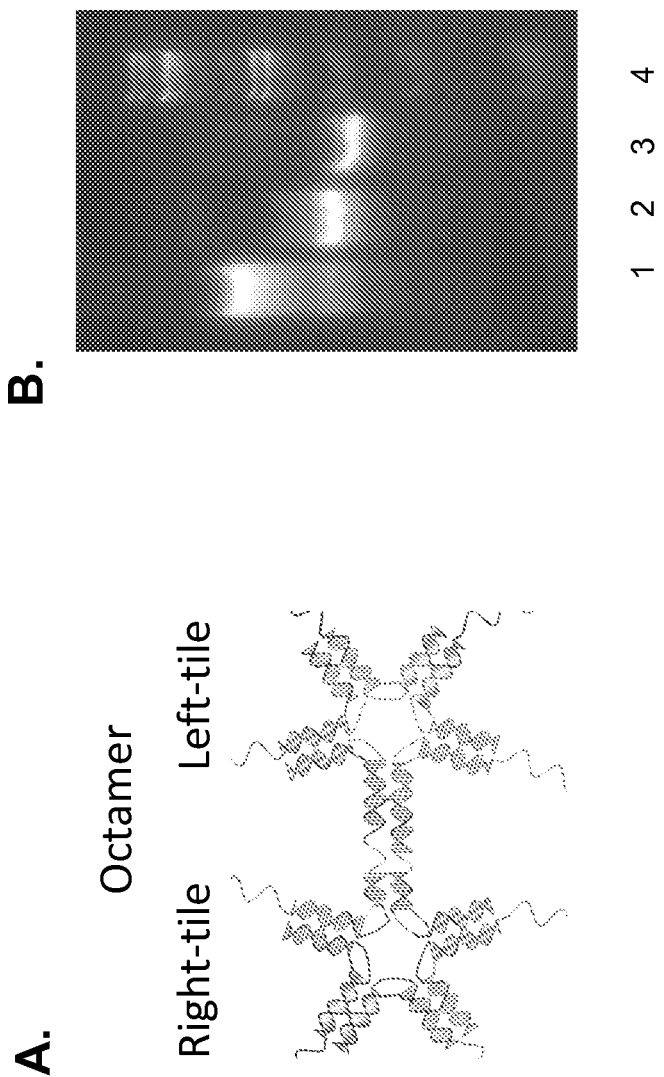
FIG. 14 shows the effects of multimeric aptamers on DNA tiles on cell-cell interaction. A) A schematic diagram of a hi-specific octameric aptamer nanostructure containing two tetrameric aptamers linked by a DNA linker. B) Photograph of image of native gel electrophoresis of the octameric aptamer tiling array or individual DNA tiles. Line 1-octamer; line 2-right-tile; line 3-left tile; and line 4-marker. C) An illustration of the results of FACS analysis indicating the occurrence of cell-cell interaction. D) Results of FACS analysis indicating the percentage of interacting B- and T-cells, over total number of B cells, as a result of aptamer-cell binding. x axis-fluorescence intensity of aptamers binding to T cells; and y-axis-fluorescence intensity of aptamers binding to B cells.
Figure 14:
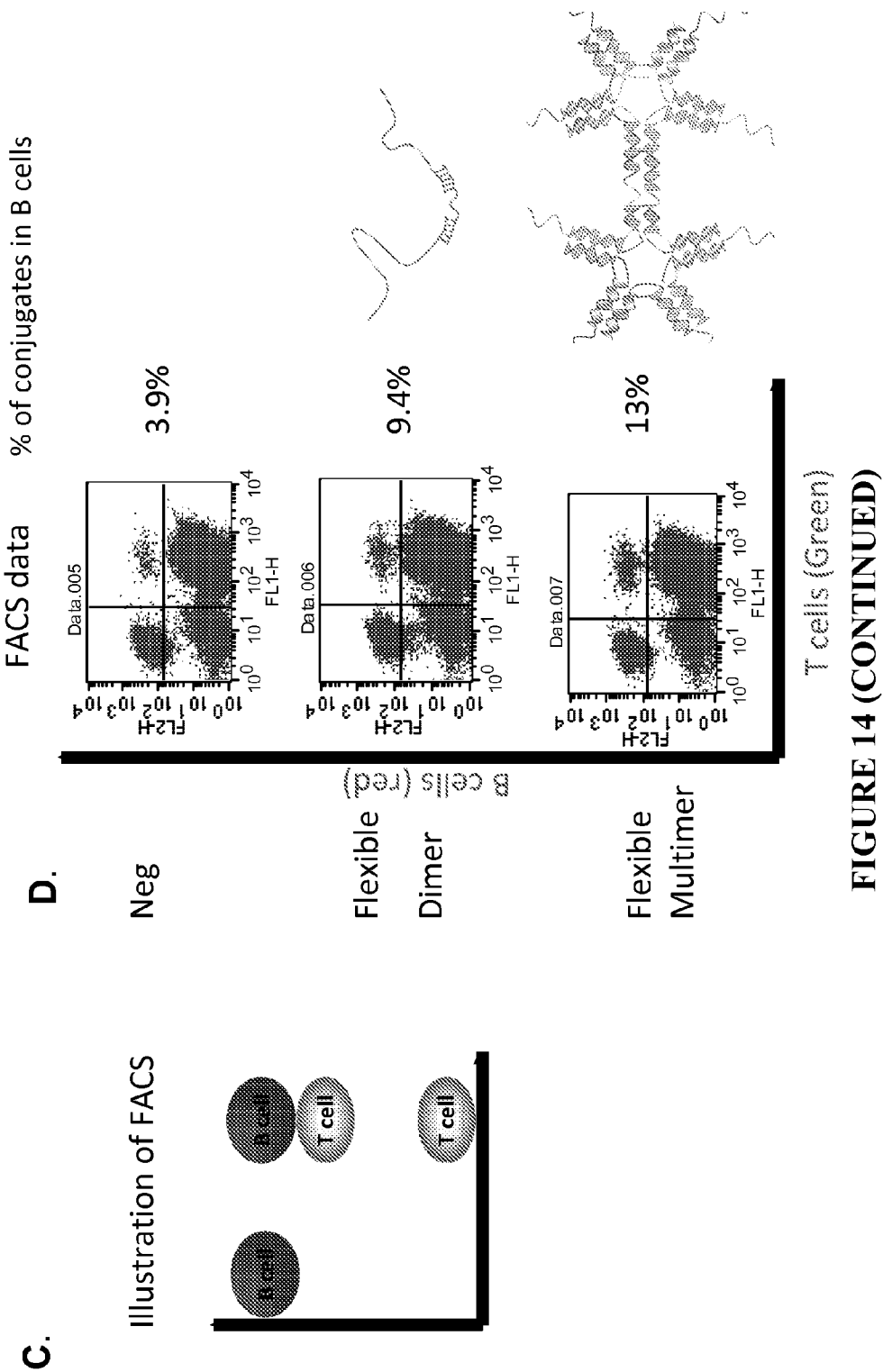

The cell-cell interaction can be detected and verified by any suitable methods in the art. For example, cell-cell interaction can result in cell aggregation. Aggregated cells can be detected based on size differential as revealed by density gradient or flow cytometry. Different types of cells can be first labeled with specific fluorescent dyes such as, without limitation, DiO and DiI (Molecular Probes, Invitrogen, Carlsbad, Calif.) and the cell aggregates can be detected by flow cytometry as illustrated in Example 2 and FIGS. 8 and 14. Cell-cell interaction can also be directly examined and verified by fluorescence microscopy. All the embodiments of this aspect can be applied in conjunction with any other aspects of the invention described herein.

In yet another aspect, the invention provides a method of treating a tumor in a mammal comprising administering to a mammal in need thereof an amount effective to treat the tumor of a composition comprising a first aptamer that is capable of binding to a receptor on an immune cell, a second aptamer that is capable of binding to a receptor on a target tumor cell, wherein the first aptamer and the second aptamer are bound to a nucleic acid nanostructure.

As used herein, the terms "treatment" and "treating" means (i) preventing the disease; for example, preventing a disease, condition or disorder in an individual who may be predisposed to the disease, condition or disorder but does not yet experience or display the pathology or symptomatology of the disease, such as preventing tumor growth and/or metastasis; (ii) limiting the disease; for example, limiting a disease, condition or disorder in an individual who is experiencing or displaying the pathology or symptomatology of the disease, condition or disorder; for example, limiting tumor growth and/or metastasis, or limiting the rate of tumor growth and/or metastasis, or extending patient survival relative to untreated patents; and (iii) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease, such as decreasing tumor size and/or incidence of metastasis. Suitable tumor cells include without limitation lymphoma cell, breast cancer cell, melanoma cell, plasmacytoma cell, sarcoma cell, glioma cell, thymoma cell, leukemia cell, prostate cancer cell, colon cancer cell, esophageal cancer cell, brain cancer cell, lung cancer cell, ovarian cancer cell, cervical cancer cell and hepatoma cell. In certain preferred embodiments, the tumor cell is leukemia cell or breast cancer cell.

Without being bound or limited to a particular mechanism, in certain embodiments, the first aptamer binds to an immune cell and the second aptamer binds to a target tumor cell, wherein the immune cell is activated by binding to the first aptamer and the target tumor cell is brought to the vicinity of the activated immune cell by the binding with the second aptamer and is killed by the activated immune cell.

In certain preferred embodiments, the immune cell is a CD4 T cell, a CD8 T cell, or an NK cell. In certain preferred embodiments, the immune cells are NK cells, and the composition further comprises NK cells, preferably NK cells derived from the mammal in need of the tumor treatment. In certain preferred embodiments, established NK cell lines of human origin are used. In other embodiments, NK cells isolated from the blood of a mammal in need of the composition are used. Methods of isolating NK cells from the blood of a mammal are known in the art; exemplary methods can be found in Binyamin, et al, 2008, Blocking NK cell inhibitory self-recognition promotes antibody-dependent cellular cytotoxicity in a model of anti-lymphoma therapy. J. Immunol. 180:6392.

NK cells are part of the innate immune system. Unlike lymphocytes that require specific antigen receptors for their interaction with targets, NK can recognize and kill viral-infected cells or tumor cells by recognizing multiple receptors that are present in damaged (e.g., infected or tumor) cells, but low or not present in normal cells. In addition, tumor cells bound by antibodies can attract NK cells to tumor cells through interactions between the bound antibodies on the tumor cells and IgG-Fc-receptors present on the NK cells. The interaction triggers cytotoxicity of NK cells, known as antibody-dependent cellular cytotoxicity (ADCC), and results in NK cell killing of the tumor cells. Suitable NK cell line includes without limitation NK92MI, an established cell line initially isolated from human acute lymphocytic leukemia.

NK-mediated cytotoxicity can be detected and measured by any suitable methods in the art. In certain preferred embodiments, NK-mediated cytotoxicity can be measured indirectly by measuring NK cell activation. In various other preferred embodiments, NK cell activation can be detected by cytokine production in the supernatant of tissue culture or cytoplasmic staining of cytokines in the cells. In alternative preferred embodiments, NK cell activation can be detected by the activation of downstream effectors, including without limitation JNK1 or ERK2 phosphorylation. In other preferred embodiments, NK cell-mediated cytotoxicity can be assayed directly by measuring apoptosis of the target tumor cells as illustrated in Example 3. Various commercially available apoptosis assaying kits can be used including without limitation CytoxiLuxPlus assay kit (OncoImmunin, Gaithersburg, Md.). It is understood to one of skill in the art that all the embodiments of this aspect can be applied in conjunction with any other aspects and embodiments of the invention.

In a further aspect, the invention provides methods of treating an immune disorder in a mammal comprising administering to a mammal in need thereof an amount effective to treat the immune disorder of a composition comprising a first aptamer that is capable of binding a receptor on an immune cell, a second aptamer that is capable of binding to a molecule or receptor on a target immune cell, wherein the first aptamer and the second aptamer are bound to a nucleic acid nanostructure. In certain preferred embodiments, the immune disorder is an autoimmune disease, asthma, or allergic reactions. In certain preferred embodiments, the first aptamer binds to an NK cell and the second aptamer binds to a surface molecule of an autoreactive immune cell. In certain preferred embodiments, the second aptamer that binds to a surface molecule of an autoreactive immune cell can be screened by cell-SELEX with autoreactive immune cells and counter-selected against normal immune cells for aptamers that bind to autoreactive immune cells but do not bind to normal immune cells. Any molecules known to be present only on the cell surface of autoimmune cells can be used, including without limitation, CD40 (NM_001250, DNA and protein sequences as shown in SEQ ID NOs:1 and 2, respectively) which is known to be associated with autoreactive B cells.

In yet another aspect, the invention provides methods of treating infection by a pathogen in a mammal comprising administering to a mammal in need thereof an amount effective to treat the infection of a composition comprising a first aptamer that is capable of binding a receptor on an immune cell, a second aptamer that is capable of binding to a molecule or receptor on an infected cell, wherein the first aptamer and the second aptamer are bound to a nucleic acid nanostructure. In certain preferred embodiments, the pathogen is a bacterium; in various other embodiments, the pathogen is a virus, or a fungus. In certain preferred embodiments, the immune cell is a CD4 helper cell; in various other embodiments, the immune cell is a CD8 cytotoxic T cell or an NK cell. In further preferred embodiments, the second aptamer binds to a surface MHC molecule on a cell infected with a pathogen. In certain preferred embodiments, the second aptamer binds microbial antigens displayed on the cell surface in the context of MHC molecules. All the embodiments of this aspect can be applied in conjunction with any other aspects of the invention.

In a further aspect, the invention provides pharmaceutical compositions comprising a composition of the invention and at least one pharmaceutically acceptable diluent, carrier and excipient. The primary vehicle or carrier in a pharmaceutical composition may be either aqueous or non-aqueous in nature. For example, a suitable vehicle or carrier for injection may be physiological saline solution, or artificial cerebrospinal fluid. Optimal pharmaceutical compositions can be determined by a skilled artisan depending upon, for example, the intended route of administration, delivery format, desired dosage and recipient tissue. See, e.g., REMINGTON'S PHARMACEUTICAL SCIENCES, supra. Such compositions may influence the physical state, stability, and effectiveness of the composition. In certain embodiments, the pharmaceutical composition further comprises NK cells.

The pharmaceutical composition to be used for in vivo administration typically is sterile and pyrogen-free. In certain embodiments, this may be accomplished by filtration through sterile filtration membranes. In certain embodiments, where the composition is lyophilized, sterilization using this method may be conducted either prior to or following lyophilization and reconstitution. In certain embodiments, the composition for parenteral administration may be stored in lyophilized form or in a solution. In certain embodiments, parenteral compositions generally are placed into a container having a sterile access port, for example, an intravenous solution bag or vial having a stopper pierceable by a hypodermic injection needle.

Once the pharmaceutical composition of the invention has been formulated, it may be stored in sterile vials as a solution, suspension, gel, emulsion, solid, or as a dehydrated or lyophilized powder. Such formulations may be stored either in a ready-to-use form or in a form (e.g., lyophilized) that is reconstituted prior to administration.

The effective amount of a pharmaceutical composition of the invention to be employed therapeutically depends, for example, upon the therapeutic context and objectives. One skilled in the art will appreciate that the appropriate dosage levels for treatment, according to certain embodiments, will thus vary depending, in part, upon the molecule delivered, the indication for which the pharmaceutical composition is being used, the route of administration, and the size (body weight, body surface or organ size) and/or condition (the age and general health) of the patient. A clinician can titer the dosage and modify the route of administration to obtain the optimal therapeutic effect. Aptamers delivered at 40-400 μg/kg have been shown to be effective in vivo. McNamara wt al., 2008. *J Clin Invest* 118:376-386

The dosing frequency depends upon the pharmacokinetic parameters of an aptamer-nucleic acid nanostructure in the formulation. For example, a clinician administers the composition until a dosage is reached that achieves the desired effect. The composition may therefore be administered as a single dose or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages may be ascertained through use of appropriate dose-response data.

Administration routes for the pharmaceutical compositions of the invention include topically, orally, through injection by intravenous, intraperitoneal, intracerebral (intra-parenchymal), intracerebroventricular, intramuscular, intra-ocular, intra-arterial, intra-portal, subcutaneous, or intra-lesional routes; by sustained release systems or by implantation devices. The pharmaceutical compositions may be administered by bolus injection or continuously by infusion, or by implantation device. The pharmaceutical composition also can be administered locally via implantation of a membrane, sponge or another appropriate material onto which the desired molecule has been absorbed or encapsulated. Where an implantation device is used, the device may be implanted into any suitable tissue or organ, and delivery of the desired molecule may be via diffusion, timed-release bolus, or continuous administration.

One of skill in the art would understand that all embodiments described herein in any aspect of the invention can be applied in any other aspects of the invention.

The Examples, which follow, are illustrative of specific embodiments of the invention, and various uses thereof. They are set forth for explanatory purposes only, and are not to be taken as limiting the invention.

EXAMPLES

Example 1

Figure 5:
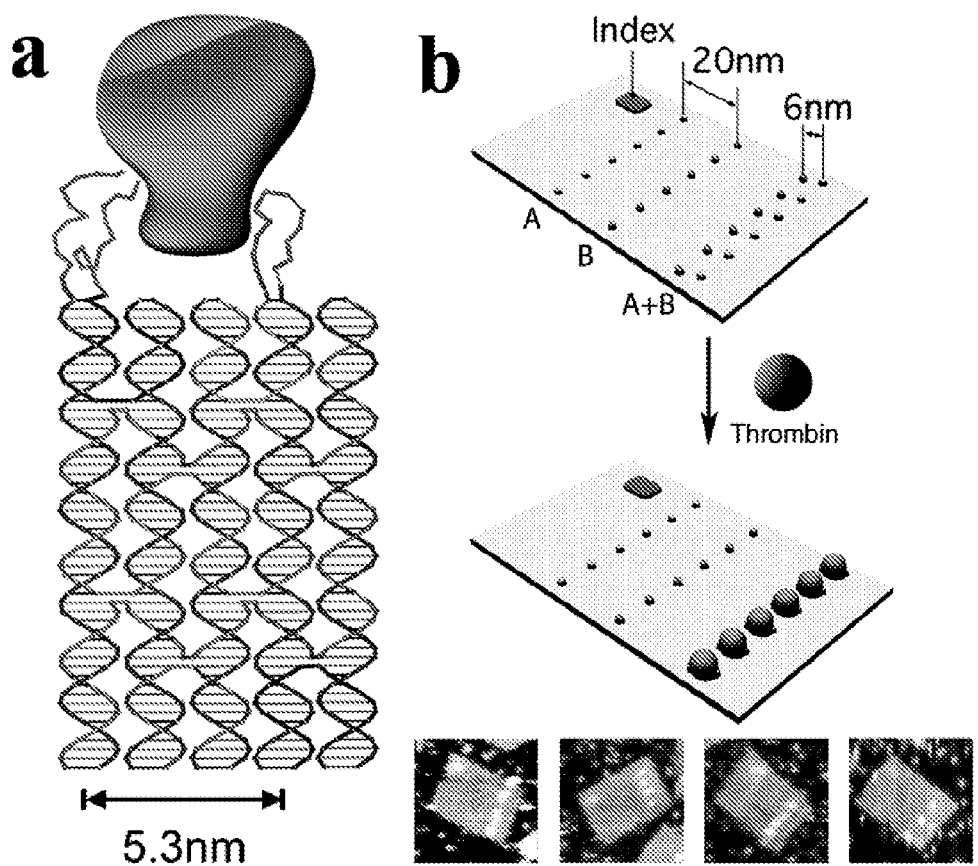
FIG. 5 shows results of multivalent binding of two aptamers to thrombin. a) Two thrombin aptamers are positioned on a five-helix DNA nanostructure at optimized distance to improve the binding efficiency. b) Single molecule visualization of the bivalent aptamer-protein binding using AFM. In this case, aptamers are displayed in lines on a rectangular shaped nucleic acid tile. The dual aptamer line possesses stronger binding affinity with protein than each individual aptamer lines.

Nanostructure Directed Assembly of Multivalent Aptamers for Enhanced Binding Affinity Multivalent interaction plays a large role in biology as many bio-machineries display high affinity multivalent bindings to their targets when sub-domains are arranged accurately with certain spatial and geometric configurations. It was demonstrated that distance dependent multivalent binding effects can be systematically investigated by incorporating multiple aptamers into self-assembled DNA nanostructures with precise control of nano-meter spatial distances. Such multivalent binding events were visualized at the single molecule level with atomic force microscopy (FIG. 5).

The results illustrate a unique application of structural DNA nanotechnology for exploring multi-component biomolecular interactions and set forth a path for constructing spatial combinatorics at the nanometer scale. This nano-engineering platform offers an unprecedented opportunity to create programmable multivalent biomolecular interactions for activation of immune responses to boost tumor immunity, as well as possible extended application with some modification for treating other diseases, such as infection, autoimmunity, asthma and allergic reactions. In certain embodiments, the first aptamer binds to an NK cell and the second aptamer binds to a surface molecule of an autoreactive immune cell. In certain embodiments, the aptamer is first selected for binding with autoreactive immune cells and counter-selected against normal immune cells. Markers for autoreactive B cells include without limitation CD40.

Example 2

Multivalent-ss-DNA Aptamers for Targeting Cell Surface Molecules

Figure 6:
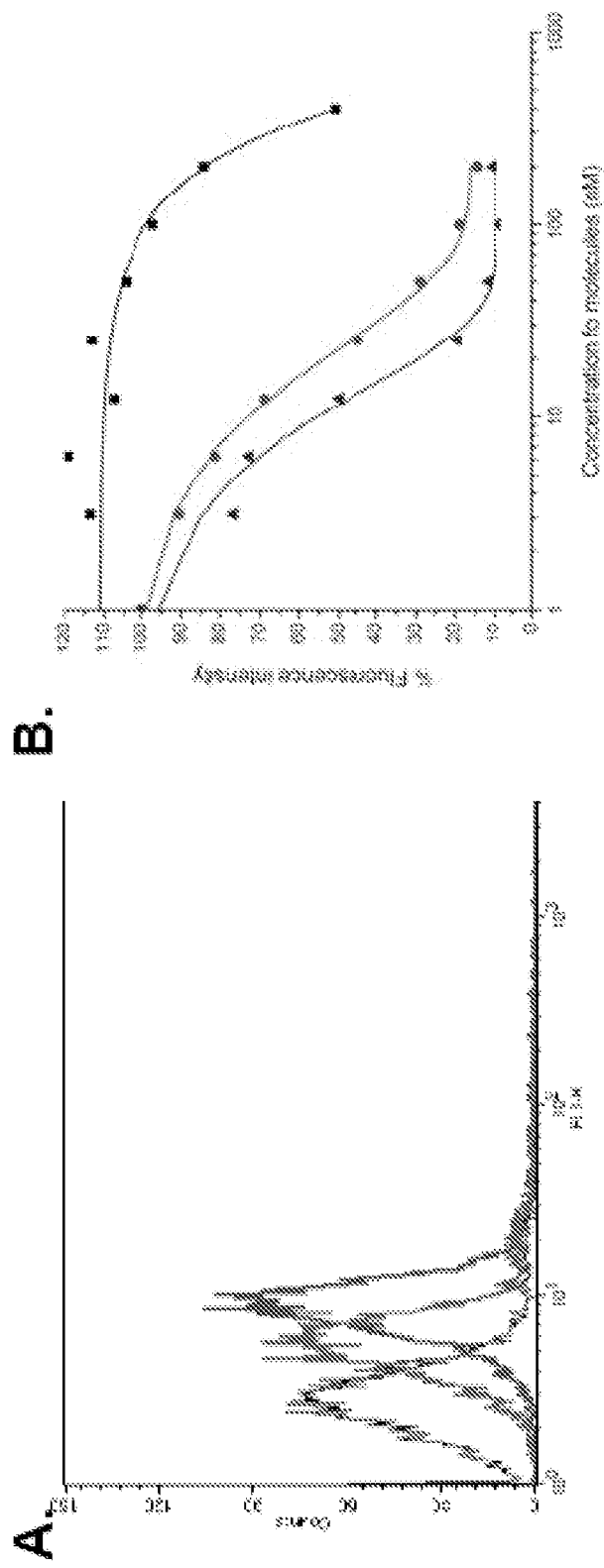
FIG. 6 shows the results of competition assays of labeled monomeric aptamers binding to a target cell by unlabeled dimeric aptamers. A) A representative profile of flow cytometry histogram indicating fluorescence intensity of the cells incubated with labeled monomeric aptamer in the presence or absence of rigid dimeric aptamers. Left peak-negative control; right peak-FITC-labeled monomeric aptamer; and middle peak-FITC-labeled monomeric aptamer and unlabeled rigid dimer (ratio 1:1). B) A graph showing does-dependent inhibition of labeled monomer binding to target cells by unlabeled monomer (square), rigid dimer (circle), or rigid tetramer (triangle).

Multimeric aptamer was constructed using a known ssDNA-aptamer (TAGGCAGTGGTTTGACGTCCGCAT-GTTGGGAATAGCCACGCCT, SEQ ID NO:3) as described by Tang et al. 2007, *Anal. Chem.* 79: 4900-4907. Dimeric and tetrameric aptamers containing such monomeric aptamer binding unit were constructed by linking monomeric aptamer with linker sequences as shown in FIG. 11A. The binding of fluorescence-labeled monomeric aptamer to a target cell was analyzed by flow cytometry. Binding competition assays were performed to assess the binding activities of various aptamer structures, i.e., monomers, dimers, trimers and tetramers to the target cells. Flow cytometry analysis was carried out measuring cell staining with the fluorescence-labeled monomeric aptamer in the presence of unlabeled dimers, trimers, or tetramers. As shown in FIG. 6A, the dimeric aptamer competed with labeled monomeric aptamer for binding to the target cells. Among various multivalent aptamers, the tetramer most effectively competed with the labeled-monomeric aptamer for binding to the target cells and thus displayed a much higher binding activity than the monomers. FIG. 6B.

The effects of the flexibility of monomeric aptamer binding units relative to the nucleic acid nanostructure on target cell binding was also examined, As shown in Table 1, the relatively rigid nanostructures appeared to further increase the binding activity, as represented by their lower IC50 valued.

TABLE 1

| IC50 of monomeric and multimeric aptamers | | | | | | |
|---|---|---|---|---|---|---|
| Aptamer | Monomer | Flexible dimer | Rigid dimer | Flexible trimer | Rigid trimer | Rigid tetramer |
| IC50/nM* | 400 | 33.0 | 22.5 | 27.8 | 20.8 | 11.6 |

*IC50: the concentration of unlabeled aptamers that resulted in 50% reduction in the binding of fluorescence-labeled monomeric aptamers to the target cells.

Figure 7:
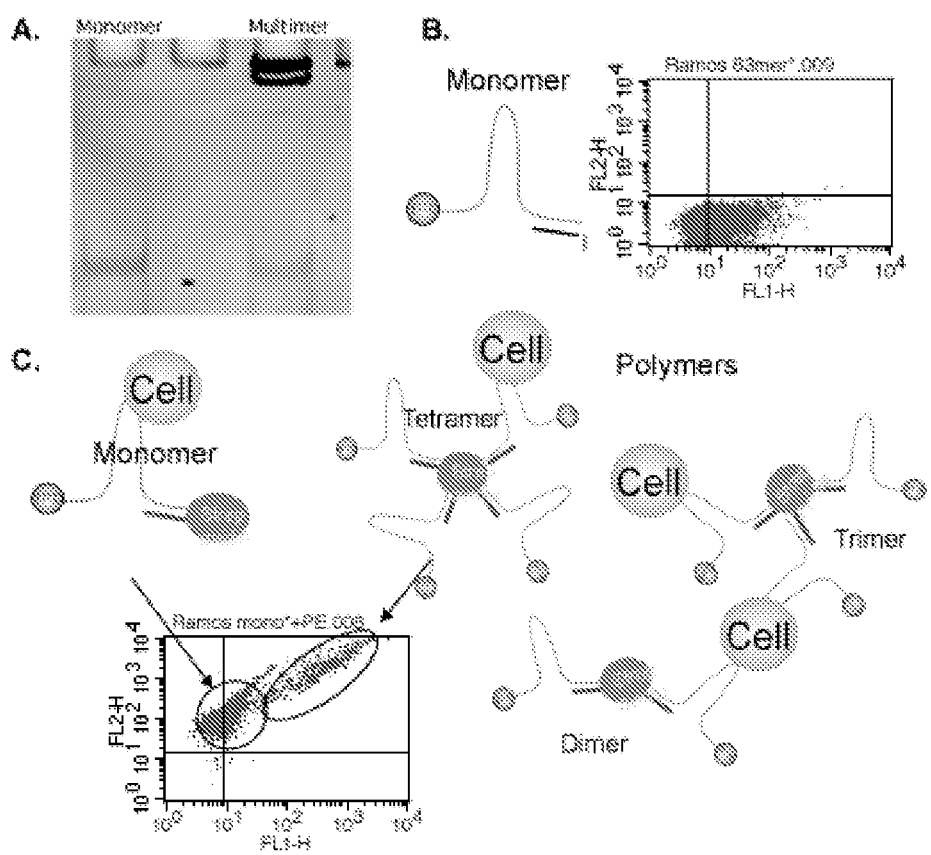
FIG. 7 demonstrates increased cellular binding of multimeric aptamer held by biotin-streptavidin interaction. A) Size analysis of monomer and streptavidin-linked polymer by gel electrophoresis; B) FACS analysis of aptamer monomer. C) FACS analysis of cells bound by Aptamer-PE labeled streptavidin.

A known ssDNA-aptamer (sequence shown in SEQ ID NO:3) that binds to human B cell leukemia cells (Ramos cells, ATCC catalog No. CRL-1596, Manassas, Va.) was used to construct multimeric aptamer through biotin-streptavidin interaction. (Tang et al., 2007, supra). Specifically, the aptamer annealed with its biotinylated primer was incubated with streptavidin-phycoerythrin (PE), in which PE was used to reveal the presence of streptavidin (FL2). The cellular binding activity was compared between single aptamer monomer and streptavidin-linked multimer. As shown in FIG. 7, a brighter FL1 signal was detected in cells stained with streptavidin-multimer as compared with cells stained with single monomers. Cells stained with multimer displayed double positive for both PE and FITC. Some of these cells also showed an elevated PE staining Given that there is only one biotin per aptamer unit, some of the enhanced PE signals can be attributed to the cellular interactions (illustrated in FIG. 7C). Thus, the results show that streptavidin-PE-aptamer multimer promoted cell-cell interactions.

Figure 8:
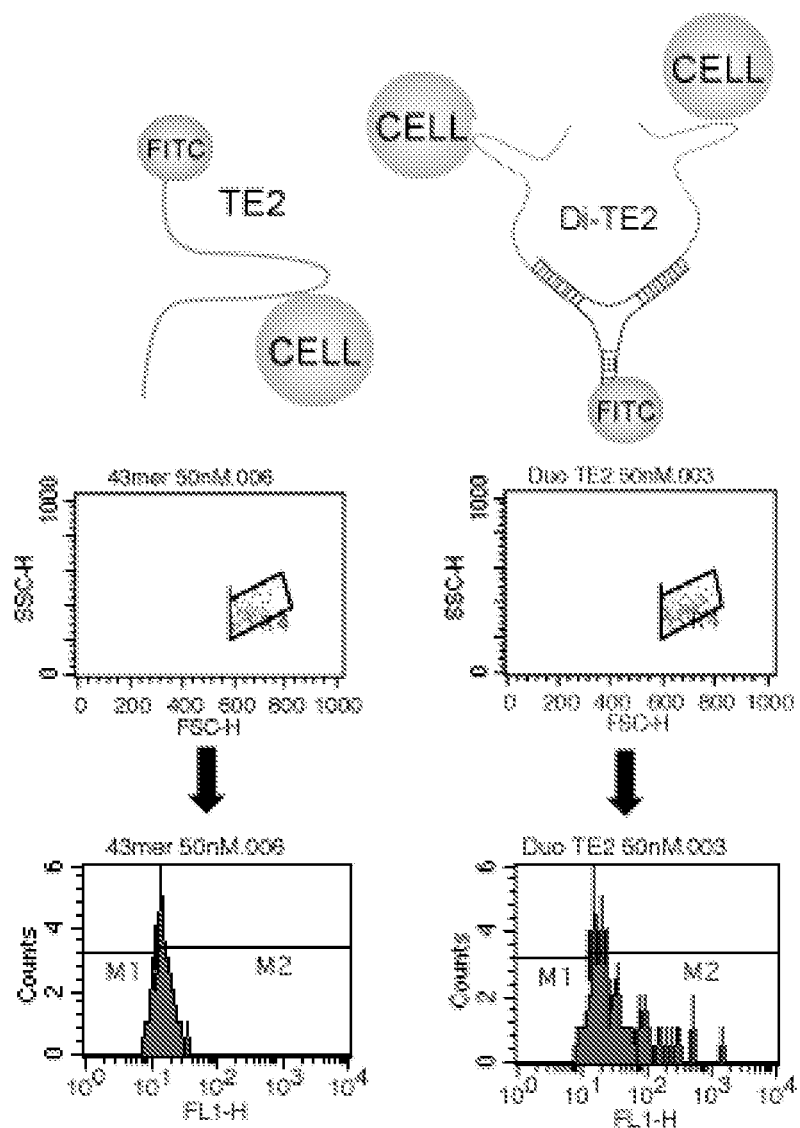
FIG. 8 shows cell aggregation engaged by dimeric, but not monomeric aptamers.

A dimeric aptamer was constructed by attaching two aptamers (sequence shown in SEQ ID NO:3) of the same type to a DNA-nanostructure as illustrated in FIG. 8. This aptamer-nucleic acid nanostructure was expected to give a similar level of FL1 signals since both monomer and dimer contain only one FITC. However, if this dimeric aptamer engaged Ramos cell-cell interaction, it would result in higher level of staining Indeed, few aggregated cell clusters, gated by the forward and size scatter, show more FITC signals (FIG. 8, right column of histograms), indicating the bridging effect of divalent aptamer. As expected, this population of cell aggregates was not observed in the sample stained with monomeric aptamer (FIG. 8, left column of histograms). Thus, the multimeric aptamer-nucleic acid nanostructure assembled by linker oligonucleotide behaved similarly to streptavidin in terms of bringing cells together and promoting cell-cell interaction.

Figure 9:
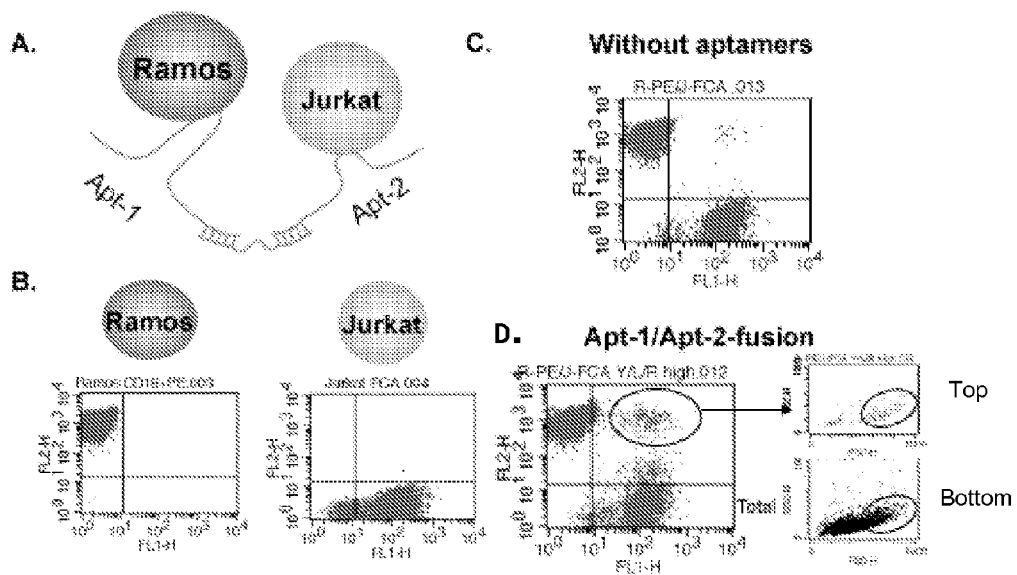
FIG. 9 shows cell-cell interactions mediated by multimeric aptamers linked by a linker polynucleotide. A) Illustration of the multimeric aptamers, and their expected cell binding; B) FACS staining profiles of pre-labeled cells (Ramos prelabeled with PE, and Jurkat prelabeled with FITC); and FACS analysis of cell mixture in the absence (C) or presence (D) of the multimeric aptamers. The PE/FITC-positive population was gated on FSC/SSC to show the cell size (FIG. 9D top panel) in comparison to the total cell distribution (FIG. 9D bottom panel).

To directly test the feasibility of multivalent aptamers in engaging cell-cell interactions, bi-specific aptamers were created using a ssDNA linker (FIG. 9A), in which one aptamer binds to Ramos cells (sequence shown in SEQ ID NO:3) and the other to Jurkat cells (ATCC catalog No. TIB-152). The Jurkat cell-specific aptamer binds to L-selectin and has the sequence 5'-TAGCCAAGGTAACCAGTACAAGG TGCTAAACGTAATGGCTTCGGCTTAC-3' (SEQ ID NO:4). The linker sequences are 5'-GCT AGT CAG ATC GTA GGT AGA CCA CGA CGA CAC ACC CTA A-3' (linker 1, SEQ ID NO:7) and 5'-GCT AGT CAG ATC GTA GGT AGT TTT TAC CAC GAC GAC ACA CCC TAA-3' (linker 2, SEQ ID NO:8). These two types of cells were pre-labeled with two different dyes, anti-CD19-PE for Ramos and vital dye (2',7'-Dichlorofluorescin diacetate, an indicator for reactive oxidative species, FITC color) for Jurkat cells. The fluorescence profiles are FL2+ for Ramos and FL1+ for Jurkat, as expected (FIG. 9B). After these cells were mixed together, they displayed single positive profiles, very few in the double-positive quadrant (compare FIG. 9C with FIG. 9B). On the other hand, after an incubation of these two cell types with bi-specific aptamer-fusion molecules, a population of cells showed positive for both PE and FITC (FIG. 9D), suggesting an association of Ramos and Jurkat cells. Further, based on the FSC and SSC analysis (FIG. 9D, right panels), a majority of these double positive cells appeared to be larger than individual Ramos or Jurkat cells, confirming the presence of Ramos-Jurkat aggregates, which were presumably mediated by the aptamer-fusion connected by the linker polynucleotide, since few such cells existed in the absence of aptamers.

Figure 10:
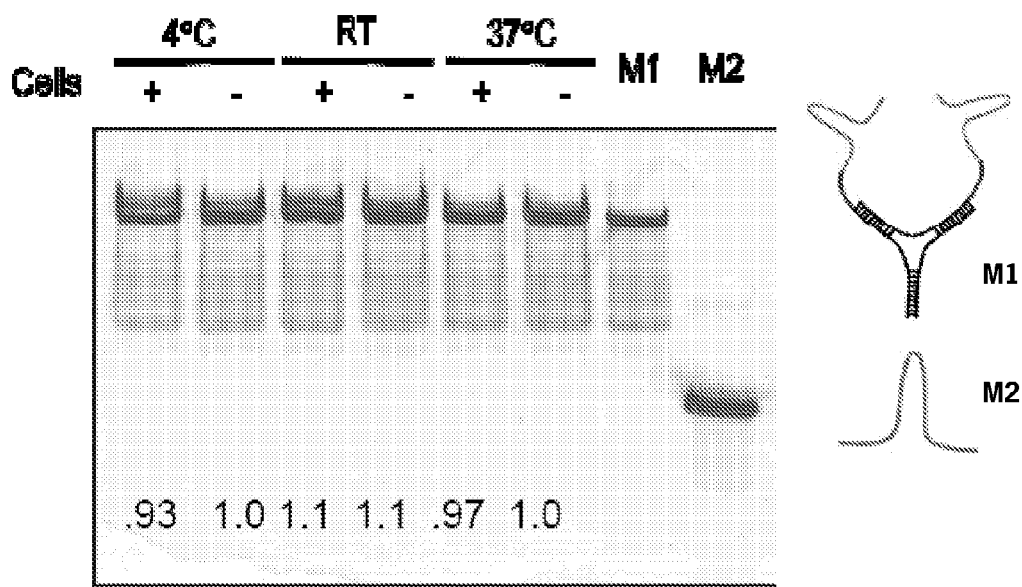
FIG. 10 shows a photograph of image of native gel electrophoresis of M1 dimeric aptamer incubated with or without cells at different temperatures. M1 and M2 are input dimeric and monomeric DNA aptamers, respectively, as illustrated on the right. The number at the bottom of each lane indicates the ratio of the recovered aptamers incubated under test conditions to those under control condition, the control condition being incubation at 4° C. in the absence of cells.

The stability and structural integrity of the nanostructures after incubating with the cells were determined. To minimize absorption and depletion of the aptamer-DNA nanostructures due to their specific binding to the cells the selected bivalent aptamer-DNA nanostructures (M1 as shown in FIG. 10) were incubated with non-target cells. The incubation was carried out at 4° C., room temperature, or 37° C. After one hour incubation, unbound aptamers were recovered from the cell mixture by spinning down the cells. The supernatants were treated with phenol: chloroform to remove proteins, and the aptamers were precipitated by 95% ethanol. The recovered aptamer DNA was dissolved in $H_2O$ and analyzed be native gel electrophoresis (16% polyacrylamide gel) to determine the levels and integrity of the aptamers. As shown in FIG. 10, the smaller bands below the migration of dimers were likely generated from incompletely annealed products during the construction of dimer rather than from degradation of formed dimers because they were also present in the input control sample (FIG. 10, M1). Thus, there bivalent aptamer-DNA nanostructures were relatively stable to withstand cell incubation.

As described below, a cell-SELEX protocol modified from the known SELEX is employed in the screening to identify aptamers that bind to NK cells or other tumor cells.

Example 3

Generation of DNA-Nanostructures with Aptamer as Novel Recognition Molecules that Engage Effector Immune Cells to Attack Tumor Cells In this series of experiments, tunable DNA nanostructures are used to create multivalent and multispecific nanostructure to promote cell-cell interactions to induce ligand-directed lymphocyte activation and tumor killing. A multimeric aptamer library is created in which multiple units of aptamers are linked together by different DNA-nanostructure. This library is screened against a well-characterized effector NK cell line (NK91MI) and tumor cell line (Ramos) to select aptamer configurations with a high binding activity to effector or tumor cells. To produce multivalent aptamer-nucleic acid nanostructures that can engage inter-cellular interactions between NK and Ramos, the identified cellular binding aptamer motif is assembled onto a programmable DNA-nanostructure platform, which is then selected on their activity to facilitate cell-cell interactions and NK-dependent cytotoxicity.

A. Tunable DNA-Nanostructure with Multivalent Aptamers for Cell Binding

Multivalent ligands are known to increase the avidity of ligand-receptor interactions. The multivalent ligands have traditionally been built from their known monomeric unit. A target-specific monomeric aptamer can be screened and identified from a random aptamer library by SELEX. This aptamer can be chemically linked to form dimeric aptamers, which would display enhanced target-binding activity as compared to its monomeric form.

A different approach is taken to create multimeric aptamer library and select multimers based on their binding to the cells of interest (i.e. using cellular SELEX), as illustrated in FIG. 11. In this case, multivalence-dependent enhanced binding becomes one of the selection requirements. The multivalent aptamer library may contain the same or different kinds of aptamers assembled on single DNA nanostructure. A multimeric aptamer with monomeric aptamer binding units that each bind to one target molecule acquire higher binding avidity than its monomeric counterpart and therefore is likely to be preferentially selected by cellular SELEX. On the other hand, multimeric aptamer with monomeric aptamer binding units that each binds different target molecules may also possess binding advantages if two or three aptamer binding motifs happen to interact with their ligands located at close vicinity on the cell surface. Interactions among these different receptor/ligand pairs can also synergize the binding activity as well. Multimeric aptamers that bind to receptor clusters, such as without limitation, an immune-synapsis that has been implicated in controlling activation status of immune cells, can be identified.

(1) Design of an Oligomeric Aptamer Library

A random aptamer library is created that can be programmed to present as dimers, trimers or tetramers (FIGS. 11A and B). A random aptamer library (either ssDNA or RNA) is modified by including oligonucleotide linkers to link individual aptamer monomers to form multimeric aptamer fusion molecules. Specifically, a random oligonucleotide library is synthesized with randomized 45 nt sequences flanked by defined 20 nt monomers to form multimeric aptamer fusion molecules. Specifically, a random oligonucleotide library is synthesized with randomized 45 nt sequences flanked by defined 20 nt sequences both upstream and downstream of the random sequence. The defined sequences are known as the 5'-arm and the 3'-arm, which are used for the amplification of selected aptamers. A linking oligonucleotide (i.e., linker) is designed to contain sequences complementary to both the 5'- and 3'-arms regions of random aptamers to form dimeric aptamers. For trimeric or tetrameric aptamers, a small trimeric or tetrameric (i.e., a Holiday junction-like) DNA nanostructure is engineered to include sequences complementary to the 3'-arm region of the random aptamers, therefore creating multimeric aptamer fusion through hybridization (as illustrated in FIG. 11A). In addition, 3 to 5 AT rich nucleotides are engineered into the linker polynucleotides as a single stranded region between the aptamer-binding motifs, which offers flexibility and freedom of multiple aptamers to coordinate and synergize multivalent interactions with cellular ligands or receptors. Various parameters are considered in the design of these aptamers as summarized in Table 2 below. Alternatively, multimeric aptamers are also formed by mixing biotinylated aptamers with streptavidin, which are included as a positive control for evaluating multimeric binding activity (as discussed above).

TABLE 2

Design of oligomeric aptamers

Number of binding motifs
Nanostructure
   Length: number and regions of complementary sequences
   Flexibility and rigidity of the structure
Distance of neighboring binding units (2-5 nm)
Rotating flexibility of binding motifs
   Number of single stranded oligonucleotides
   Selection and combination of A/T (2) Selection of Multimeric Aptamers to NK Cells or Tumor Cells A modified cellular SELEX procedure is employed to select target-binding aptamers as illustrated in FIG. 11C. Because of its multimeric form, an individual aptamer fusion molecule may have multivalent but single binding specificity, or multivalent and multi-specific binding activity. Both types of these aptamer molecules are desirable as long as they display high binding avidity to target cells. For example, if aptamers with mixed specificities are selected by cellular binding, their corresponding cellular receptors likely reside in close vicinity on the cell surface or belong to different regions of the same surface molecules. These types of aptamers are most likely present in the initial random library or during the early stage of cellular SELEX selection. Multi-specific aptamers that survive rounds of selection should have the advantage of targeting several co-receptors and therefore triggering multiple signaling pathways for cellular activation. On the other hand, multivalent but single specific target-binding aptamers are expected to be more readily selected by the cellular SELEX because of their intrinsic high binding avidity. This type of aptamer molecules can be used to target both tumor cells and effector cells.

To ensure the quality of the selected aptamers for subsequent construction of bi-specific aptamer fusion (see below), both ssDNA and RNA SELEX approaches can be applied to increase the chances of identifying aptamers with optimal binding activity and stability to NK or Ramos cells. For ssDNA aptamer selection, the oligomeric aptamer library is incubated with a NK cell line, NK92MI (ATCC No. CLR-2408) following the cellular SELEX procedure. The aptamers that binds to NK cells are counter-selected against the B cell lymphoma Ramos cell line. The selected aptamers are PCR amplified using 5'-arm sequences and the biotinylated oligonucleotides that are complementary to the 3'-arm. The ssDNA isolated from the PCR products is incubated with the linker polynucleotides to form multimeric aptamers and then allowed for subsequent selection and amplification.

For the selection of target specific RNA-aptamers, a well-established RNA-aptamer selection protocol (Ohuchi, S. P., T. Ohtsu, and Y. Nakamura. 2006. Selection of RNA aptamers against recombinant transforming growth factor-beta type III receptor displayed on cell surface. *Biochimie* 88:897-904) is followed with some modification. The dsDNA after PCR amplification of the random DNA library is transcribed to generate a RNA pool using T7-RNA polymerase. This RNA library is incubated with multimeric linkers to form multivalent aptamer library. After incubation of the library with NK92MI cells, RNA-aptamers bound to NK92MI cells are counter-selected with Ramos cells. Then, the selected RNAs are reversely transcribed into cDNAs and amplified by PCR, which are transcribed into RNA molecules. These RNA molecules are incubated with linkers to form multivalent aptamers for the next round of selection and amplification. Aptamers of ssDNA or RNA aptamers labeled with fluorophore are used to reveal aptamer-specific cell binding by flow cytometry. Furthermore, the aptamers that bind to NK cells can also be enriched through FACS-based cell sorting. After 20-30 cycles of positive/negative selection, the selected aptamers (less than 20 different kinds) are cloned and sequenced. The binding valence and specificity of selected multimeric aptamer is further characterized. For example, the binding aptamers are eluted from the cells and analyzed by gel electrophoresis for the size and species, some of which are analyzed by sequence analyses.

The Ramos cell line is used as the tumor target as it displays a low level of natural lysis by NK92 cells, which allows the selection of aptamer-fusion that can induce NK's cytotoxicity against tumor cells. In addition, a pre-B cell leukemia line (Reh, ATCC catalog No. CRL-8286) can also serve as a tumor target. For a broader application of these aptamers, especially in vivo application, a more stringent specificity is demanded for the tumor-specific aptamers to minimize bystander killing, i.e., selecting for the lack of binding to normal peripheral blood mononuclear cells (PBMC). Therefore, a dose-dependent binding activity of selected aptamers is examined in various cell lines, as well as in normal PBMC, to ensure that these aptamers bind to tumor cells, but not to effectors or PBMC.

(3) Modification of Selected Aptamers to Improve their Stability and Binding Avidity For their ultimate in vivo application, aptamers need to be stable in an environment full of proteins and enzymes. Modifications are conducted after identification of suitable effector- and tumor-specific aptamers (Keefe, A. D. et al. SELEX with modified nucleotides. *Curr Opin Chem Biol* 12:448-456). In the case of DNA aptamers, phosphorothioate is incorporated into the backbone of ssDNA synthesis. Alternatively, 5'-modified pyrimidine can also be included in the synthesis. For RNA aptamers, modified nucleotides can also be considered in the RNA synthesis, such as substitutions of the 2'-OH groups of the ribose backbone, e.g., with 2'-deoxy-NTP or 2'-fluoro-NTP, using T7 RNA polymerase mutant (Epicentre Biotech, Madison, Wis.). The resistance of these modified aptamers to nuclease is tested by incubating them with nucleases or mouse serum that may contain nucleases and the integrity of aptamers is analyzed by gel electrophoresis. Finally, the modified aptamers are tested for cell binding using both flow cytometry and confocal fluorescent microscopy imaging to ensure that the modification does not compromise the cell binding activity.

(4) Evaluation of NK-Specific Aptamers for their Activity in Inducing NK Activation It has been demonstrated that the cytotoxicity induced by cross-linking of NK-activating receptors is usually mediated through signal transduction pathway of ERK2 and JNK1 (Chen, X. et al. Many NK cell receptors activate ERK2 and JNK1 to trigger microtubule organizing center and granule polarization and cytotoxicity. *Proc Natl Acad Sci USA* 104: 6329-6334, Li, C. et al. 2008. JNK MAP kinase activation is required for MTOC and granule polarization in NKG2D-mediated NK cell cytotoxicity. *Proc Natl Acad Sci USA* 105: 3017-3022). Thus, activation of these signaling pathways by any targeting ligands is a reflection of their potential in activating NK cells' killing activity. This characteristic of NK activation can be utilized to screen the selected aptamers and to determine whether they can induce ERK2 and JNK1 phosphorylation of NK92 cells.

Figure 12:
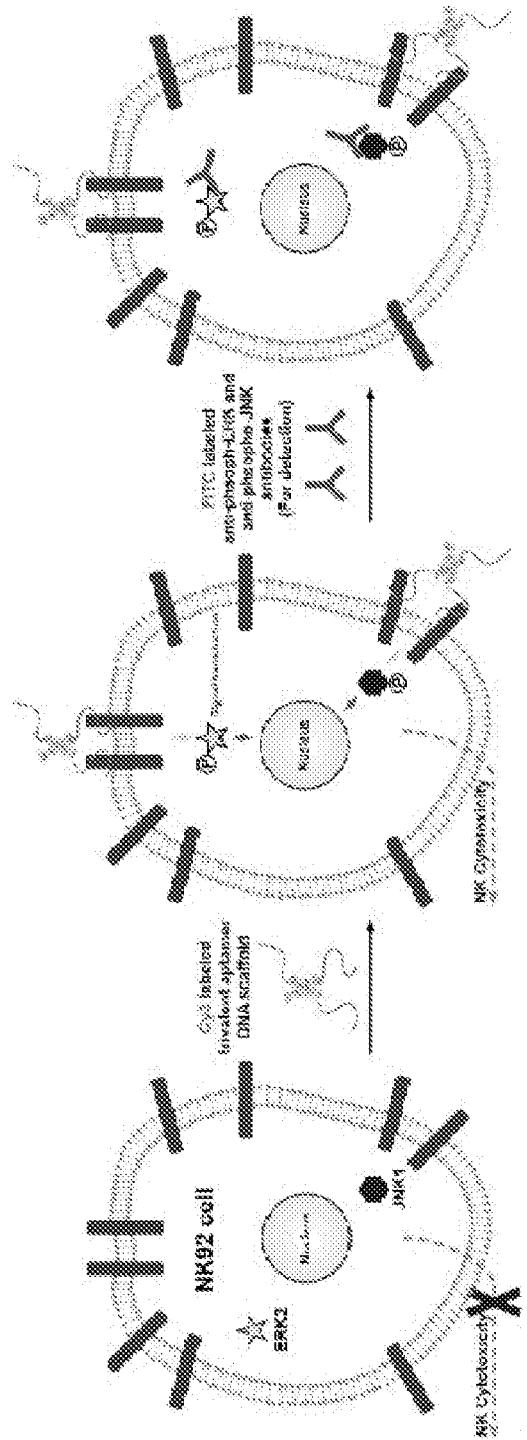
FIG. 12 illustrates NK cell activation induced by multivalent aptamers. Cells are incubated with fluorophore-conjugated aptamers, and the activation of the cells is monitored using fluorescence-labeled anti-phosphorylated JNK/ERK antibodies.

FITC-conjugated multivalent aptamer-nucleic acid nanostructure is incubated with NK92 for 10 min at room temperature, and the cells are harvested for intracellular staining with phycoerythrin (PE)-labeled anti-phospho-ERK and anti-phospho-JNK antibodies. FIG. 12. These cells are then analyzed by flow cytometry, using excitation at 488 nm, and two emissions for displaying the dual staining, i.e., FL1 for FITC and FL2 for PE. Antibodies specific to NK activation receptors (such as anti-LFA-1 antibody) are included as a positive control for activation of ERK and JNK phosphorylation (Barber, D. F. et al. 2004. LFA-1 contributes an early signal for NK cell cytotoxicity. *J Immunol* 173:3653-3659). The presence of double-positive cells for both PE and FITC reflects the stimulation of NK activation by NK-binding aptamers. Multimeric aptamer comprising PE-labeled streptavidin and biotinylated monomeric aptamers binding units are also tested for their activity in NK cell activation. Using this screening procedure, whether the selected aptamers can activate the signaling pathways critical to NK activation (i.e., based on cell binding) can be determined (FIG. 12). The multimeric aptamers demonstrating this activity are chosen for subsequent construction of multivalent and multi-specific aptamer nanostructures.

By combining SELEX technology with the tunable DNA-nanostructure platform, a multimeric aptamer library can be created and integrated with the selection scheme based on naturally existing multivalent interactions. For a proof-of-concept construction, only the selection of aptamers that bind to NK92MI and Ramos cells is performed. However, it is understood by one of skill in the art that the concept introduced herein can be applied to other cell-cell interactions.

Many surface markers on NK cells are known to function as negative regulators. Therefore, the aptamers that bind to NK may not always function as activators. To weed out "negative aptamers", an NK-killing assay is carried out, in which K562 (ATCC catalog No. CCL-243), an NK-sensitive target cell line that can be directly lysed by NK92, is used. In the assay, the cytotoxicity of NK cells is examined by measuring apoptosis-dependent conversion of fluorogenic caspase substrates (Packard, et al, 2007. Granzyme B activity in target cells detects attack by cytotoxic lymphocytes. *J Immunol* 179:3812). The aptamer that causes inhibition of NK-mediated killing of K562 is excluded from the subsequent construction of bispecific aptamer-fusion (See below). This concept can also be employed in other cell-cell interactions.

B. Addressable DNA-Nanostructure to Form Bispecific Aptamer Fusion for Effector-Target Interactions Various DNA nano-structures are available for the systematic study of inter-cellular interactions. It has been demonstrated that different proteins can be organized in a highly ordered fashion using the DNA directed self-assembly strategy (Chhabra, R. et al. 2007. Spatially addressable multiprotein nanoarrays templated by aptamer-tagged DNA nanoarchitectures. *J Am Chem Soc* 129:10304-10305). The same technique can be applied here to create bispecific aptamer array for engaging effector-target interactions. For this purpose, individual cell targeting aptamers are incorporated into the addressable self-assembled DNA nanostructures. Each type of aptamers are assigned a unique position to accommodate the inter-cellular distance and orientation.

(1) Various Design of DNA Nanostructure to Construct Aptamer-Nucleic Acid Nanostructure that Bridges Two Types of Cells This construction can be precisely controlled by placing cell-binding aptamers on an addressable DNA nanostructure. Here, the distance between two aptamers can be tuned in a closed-up and step-wise fashion. FIG. 13A shows a possible design using multi-helical bundle DNA to display multi-specific aptamers. The two different sets of aptamers can be positioned at the opposite ends of helical bundles, making it possible to arrange two different types of cells along aptamers that bind to each different cell type. Such DNA nanostructure is expected to be rigid enough to hold the relatively "heavy" cells and fix their spatial positions.

Alternatively, a "DNA origami", a fully addressable DNA nanoarray made by folding M13 genomic DNA by hundreds of short oligonucleotides (also known as staple strands), is suitable to create multivalent and multispecific cell binding platform (FIG. 13B) (Park, S. H. et al. 2005. Programmable DNA self-assemblies for nanoscale organization of ligands and proteins. *Nano Lett* 5:729-733). Different configurations of DNA origami with defined position and spatial distances of aptamers are tested for cellular engagement. FIG. 13C-D illustrated exemplary aptamer-nucleic acid nanostructures for promoting Ramos-NK interactions using a rectangular shaped origami carrying two types of multivalent aptamers. For instance, the distance between the same types of aptamers can be adjusted in the range of 2-5 nm, approximating optimal distance for cross-linking neighboring receptors to activate cells. Similarly, the distance between different sets of aptamers for cell-cell interactions can be tuned from 15 to 20 nm, to direct effector cells to target cells. Likewise, the multi-specific aptamers-nucleic acid nanostructure can have multivalent aptamers positioned on the opposite faces of the DNA origami to test engagement and inter-cellular interactions for induction of functional activation of effector cells (FIG. 13D).

(2) Examination of Cell-Cell Interactions Mediated by Multimeric Aptamer DNA-Nanostructure To assess whether the designed multimeric-aptamers can engage interactions between effector cells and tumor cells, an aggregation assay established for visualization of NK interaction with their target cells is used. Specifically, NK-92 and Ramos cells are labeled with two different vital dyes (DiO and DiI, Molecular Probes, Invitrogen, Carlsbad, Calif.) to mark cells with distinctive fluorescent colors. These labeled cells are mixed together in the absence or presence of multimeric-aptamers at various concentrations. After 20 min incubation at 4° C., the cell suspension is washed and fixed in 1% paraformaldehyde to retain conjugated cells. The cell mixture is analyzed by flow cytometry, in which aggregated cells are in larger size and dual positive for the labeling as reported previously (Li, C. et al. 2008, JNK MAP kinase activation is required for MTOC and granule polarization in NKG2D-mediated NK cell cytotoxicity. *Proc Natl Acad Sci USA* 105: 3017-3022, Radcliff, G. et al. 1991, Quantification of effector/target conjugation involving natural killer (NK) or lymphokine activated killer (LAK) cells by two-color flow cytometry. *J Immunol Methods* 139:281-292, Papa, S. et al. 1994, Functional NK assays using flow cytometry. *Methods Cell Biol* 42 Pt B:193-207). As a positive control, the cell mixture is treated with polyethylene glycol to induce cell-cell fusion. Cell-cell interactions are also examined by the fluorescence microscopy to determine the number and distribution of the cell types in the cluster. The specificity of multi-specific-aptamer nanostructures in mediating aggregate formation is determined by including monomeric aptamers that bind to either effectors or tumors. The inclusion of monomeric aptamers interferes and disrupts the formation of cell aggregates by competing with the aptamer nucleic acid nanostructure for the binding sites on the cell surface.

Using these procedures, several parameters relative to the design are evaluated and modified if necessary. For example, various DNA-nanostructures that present different valences, orientation and configuration of aptamer binding units are tested for the sensitivity and stability of the multimeric aptamers in engaging NK cells to tumor cells. In addition, different effector cells-to-target cells ratios during cell incubation are also examined in the formation of cell aggregates.

The activity of dimeric vs. tetrameric bi-specific aptamers in promoting interaction of two different types of cells was analyzed. FIG. 14A illustrates the structure of an octamer, or a bi-specific multimeric aptamer nucleic acid nanostructure containing two bi-specific tetrameric aptamers each with binding specificity to two different cell types. FIG. 14B demonstrates gel mobility of the bi-specific multimeric aptamer nucleic acid nanostructures (lane 1) the right tiles (lane 2) and the left tiles (lane 3). FIG. 14C is a schematic illustration of fluorescence-stained cells in the presence of bi-specific aptamer nanostructure. Specifically, if the aptamer nanostructures can bind to both cell types (T and B cells labeled with green and red fluorescence tags, respectively), the T- and B-cell aggregates would appear in the upper-right quadrant of the FACS data. FIG. 14D is one representative of such analyses. Pre-labeled T and B cells were mixed together in the absence (top), the presence of dimeric aptamer nanostructures (middle) or the presence of tetrameric aptamer nanostructures (bottom), and analyzed by flow cytometry. Tetrameric aptamer nanostructures resulted in the highest percentage of aggregated cells (13%, the number of B cells in the T- and B-cell aggregates over total B cells), higher than the dimeric aptamer nanostructures (9.4%). This data indicates that increased binding valence of bi-specific aptamers enhanced cell-cell interaction between two different types of cells.

(3) Determination of NK-Targeted Killing of Tumor Cells Induced by Bi-Specific Aptamer DNA-Nanostructure NK-mediated cytotoxicity of tumor cells can be detected in real-time by apoptosis-dependent conversion of fluorogenic caspase substrates, which has been formulated as CytoxiLux-PLus assay kit (OncoImmunin, Gaithersburg, Md.) (Packard, B. Z. et al. 2007. Granzyme B activity in target cells detects attack by cytotoxic lymphocytes. *J Immunol* 179:3812-3820). The kit contains cell-labeling dye (red) and fluorogenic caspase substrate (green). Tumor cells (i.e., Ramos or Reh) are pre-labeled with red-vital dye to distinguish them from unlabeled effector cells (i.e., NK92MI). Upon NK-mediated cytotoxicity, cell-permeable fluorogenic caspase-3 substrates inside the target cells are converted by activated caspase-3 into fluorescent peptides (green). Thus, apoptotic tumor cells are marked as dual positive for both red and fluorescein-peptide green, and revealed by flow cytometry under FL2 and FL1, respectively.

Based on the procedure, the aptamer-nucleic acid nanostructure that bridges two types of cells is tested for its ability to increase NK-mediated cytotoxicity. The aptamer-nucleic acid nanostructure-mediated cytotoxicity is examined and confirmed by including in the reaction aptamers that bind to either tumor cells alone or effector cells alone to see whether the cytotoxicity mediated by the tested aptamer-nucleic acid nanostructure is interfered. To increase the specificity of aptamer-mediated cytotoxicity, lower effector: tumor ratios are used. An NK-sensitive cell line, K562, is included as a positive control for cytotoxicity analysis, as it can be lysed by NK cells directly.

Figure 15:
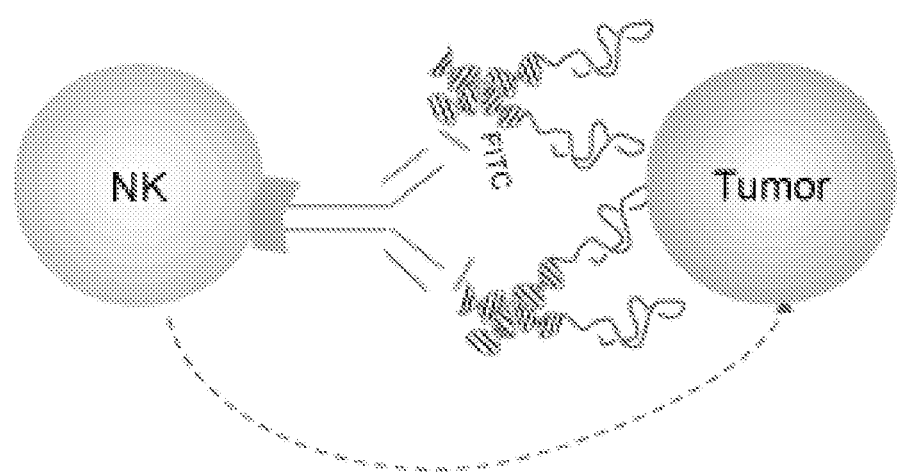
FIG. 15 shows a schematic illustration of NK-mediated cytotoxicity by aptamer-IgG-fusion, in which anti-FITC antibody binds to the FITC-labeled aptamer that binds to tumor cells.

To assess how the NK-tumor bridging aptamer-nanostructures affect the NK activation status other than increasing NK cytotoxicity, cytokine production from the cells is measured, either by analyzing the supernatant of the cell culture or performing cytoplasmic staining of cytokines in conjunction with phenotyping of NK cells. Alternative NK-binding molecules other than aptamers are also tested. For example, NK activation receptor FcgIIIR (CD16, NM_001127593, DNA and protein sequences as shown in SEQ ID NOs:5 and 6, respectively) interacts with IgG-coated cells, the interaction of which triggers NK cell activation and killing of target cells. Such antibody-dependent cellular cytotoxicity (ADCC) has been explored for creating bi-specific antibody to engage NK cells to target tumor cells (Ferrini, S. et al. 1991. Bispecific monoclonal antibodies directed to CD16 and to a tumor-associated antigen induce target-cell lysis by resting NK cells and by a subset of NK clones. *Int J Cancer* 48:227-233). For this purpose, a CD16 gene that encodes a high-affinity FcgIIIR is introduced into NK92MI cells that are CD16-negative. Then, IgG molecules are linked to target cell-specific aptamers in a manner that the IgG-Fc region is exposed for binding to CD16 on the surface of NK cells. This IgG-aptamer fusion can bridge target cells to NK cells for targeted killing (FIG. 15). To create a direction linkage of IgG molecules with target-specific aptamer, anti-fluorescein (FITC) antibody and FITC-conjugated aptamers can be used to facilitate assembly of the Fc-aptamer DNA nucleic acid nanostructure, which is tested for NK-mediated cytotoxicity.

The functional activity of the tumor-killing aptamer-nanostructures is tested in vivo using tumor-bearing mice. In this system, the structural stability, toxicity and efficacy in inhibiting tumor growth of these nanostructures is evaluated. For this set of experiments, tumor (Ramos) cells are inoculated into severe combined immunodeficient (scid) mice as they do not mount immune responses against tumor graft. Then, the aptamer-nanostructures with aptamers that bind to NK-91MI cells and Ramos cells, and optionally in combination with NK-92MI cells, are introduced into these tumor-bearing mice to assess their ability to reduce tumor growth in scid mice (Tonn, T. et al. 2001. Cellular immunotherapy of malignancies using the clonal natural killer cell line NK-92. *J Hematother Stem Cell Res* 10:535-544). In addition, other immune modulating ligands can be included to create nanoscale aptamer-complexes that mobilize multiple signaling pathways and synergize immune responses against tumor cells in vivo.

It should be understood that the foregoing disclosure emphasizes certain specific embodiments of the invention and that all modifications or alternatives equivalent thereto are within the spirit and scope of the invention as set forth in the appended claims.

What is claimed is:

1. A composition comprising a first aptamer that is capable of binding to a receptor of a first cell type, a second aptamer that is capable of binding to a receptor of a second cell type, wherein the first and second ligands are each bound to a nucleic acid nanostructure, wherein the nucleic acid nanostructure comprises a nucleic acid tile.

2. The composition of claim 1, wherein the distance between the first aptamer and the second aptamer on the nucleic acid nanostructure is about 15-20 nm.

3. The composition of claim 2, wherein the first aptamer comprises a plurality of first aptamers, and the second aptamer comprises a plurality of second aptamers.

4. The composition of claim 3 wherein the distance between each aptamer of the plurality of first aptamers and the distance between each aptamer of the plurality of second aptamers on the nucleic acid nanostructure is about 2 nm to about 5 nm.

5. The composition of claim 4 wherein the first aptamer and the second aptamer are each present on the aptamer-nucleic acid nanostructure at a density of 4-9 aptamers per aptamer-nucleic acid nanostructure.

6. The composition of claim 1, wherein the aptamer-nucleic acid nanostructure is between 10 nm and 100 nm in length.

7. The composition of claim 1, wherein the first aptamer comprises a multimer of an aptamer that is capable of binding to a receptor of the first cell type, and/or the second aptamer comprises a multimer of an aptamer that is capable of binding to a receptor of the second cell type.

8. The composition of claim 7, wherein the first aptamer comprises a plurality of first aptamers, and the second aptamer comprises a plurality of second aptamers.

9. The composition of claim 8 wherein the distance between each aptamer of the plurality of first aptamers and the distance between each aptamer of the plurality of second aptamers on the nucleic acid nanostructure is about 2 nm to about 5 nm.

10. The composition of claim 1, wherein the nucleic acid nanostructure comprises a plurality of nucleic acid tiles.

11. The composition of claim 1, further comprising a pharmaceutically acceptable carrier.

* * * * *

SEQUENCE LISTING

<160> NUMBER OF SEQ ID NOS: 8

<210> SEQ ID NO 1
<211> LENGTH: 1616
<212> TYPE: DNA
<213> ORGANISM: Homo sapiens
<220> FEATURE:
<221> NAME/KEY: CDS
<222> LOCATION: (78)..(911)

<400> SEQUENCE: 1

```
gccaaggctg gggcagggga gtcagcagag gcctcgctcg ggcgcccagt ggtcctgccg        60
cctggtctca cctcgct atg gtt cgt ctg cct ctg cag tgc gtc ctc tgg         110
                   Met Val Arg Leu Pro Leu Gln Cys Val Leu Trp
                    1               5                  10 ggc tgc ttg ctg acc gct gtc cat cca gaa cca ccc act gca tgc aga        158
Gly Cys Leu Leu Thr Ala Val His Pro Glu Pro Pro Thr Ala Cys Arg
             15                  20                  25 gaa aaa cag tac cta ata aac agt cag tgc tgt tct ttg tgc cag cca        206
Glu Lys Gln Tyr Leu Ile Asn Ser Gln Cys Cys Ser Leu Cys Gln Pro
         30                  35                  40 gga cag aaa ctg gtg agt gac tgc aca gag ttc act gaa acg gaa tgc        254
Gly Gln Lys Leu Val Ser Asp Cys Thr Glu Phe Thr Glu Thr Glu Cys
     45                  50                  55 ctt cct tgc ggt gaa agc gaa ttc cta gac acc tgg aac aga gag aca        302
Leu Pro Cys Gly Glu Ser Glu Phe Leu Asp Thr Trp Asn Arg Glu Thr
 60                  65                  70                  75 cac tgc cac cag cac aaa tac tgc gac ccc aac cta ggg ctt cgg gtc        350
His Cys His Gln His Lys Tyr Cys Asp Pro Asn Leu Gly Leu Arg Val
                 80                  85                  90 cag cag aag ggc acc tca gaa aca gac acc atc tgc acc tgt gaa gaa        398
Gln Gln Lys Gly Thr Ser Glu Thr Asp Thr Ile Cys Thr Cys Glu Glu
             95                 100                 105 ggc tgg cac tgt acg agt gag gcc tgt gag agc tgt gtc ctg cac cgc        446
Gly Trp His Cys Thr Ser Glu Ala Cys Glu Ser Cys Val Leu His Arg
        110                 115                 120 tca tgc tcg ccc ggc ttt ggg gtc aag cag att gct aca ggg gtt tct        494
Ser Cys Ser Pro Gly Phe Gly Val Lys Gln Ile Ala Thr Gly Val Ser
    125                 130                 135 gat acc atc tgc gag ccc tgc cca gtc ggc ttc ttc tcc aat gtg tca        542
Asp Thr Ile Cys Glu Pro Cys Pro Val Gly Phe Phe Ser Asn Val Ser
140                 145                 150                 155 tct gct ttc gaa aaa tgt cac cct tgg aca agc tgt gag acc aaa gac        590
Ser Ala Phe Glu Lys Cys His Pro Trp Thr Ser Cys Glu Thr Lys Asp
                160                 165                 170 ctg gtt gtg caa cag gca ggc aca aac aag act gat gtt gtc tgt ggt        638
Leu Val Val Gln Gln Ala Gly Thr Asn Lys Thr Asp Val Val Cys Gly
            175                 180                 185 ccc cag gat cgg ctg aga gcc ctg gtg gtg atc ccc atc atc ttc ggg        686
Pro Gln Asp Arg Leu Arg Ala Leu Val Val Ile Pro Ile Ile Phe Gly
        190                 195                 200 atc ctg ttt gcc atc ctc ttg gtg ctg gtc ttt atc aaa aag gtg gcc        734
Ile Leu Phe Ala Ile Leu Leu Val Leu Val Phe Ile Lys Lys Val Ala
    205                 210                 215 aag aag cca acc aat aag gcc ccc cac ccc aag cag gaa ccc cag gag        782
Lys Lys Pro Thr Asn Lys Ala Pro His Pro Lys Gln Glu Pro Gln Glu
220                 225                 230                 235 atc aat ttt ccc gac gat ctt cct ggc tcc aac act gct gct cca gtg        830
Ile Asn Phe Pro Asp Asp Leu Pro Gly Ser Asn Thr Ala Ala Pro Val
                240                 245                 250
```

-continued

```
cag gag act tta cat gga tgc caa ccg gtc acc cag gag gat ggc aaa     878
Gln Glu Thr Leu His Gly Cys Gln Pro Val Thr Gln Glu Asp Gly Lys
            255                 260                 265 gag agt cgc atc tca gtg cag gag aga cag tga ggctgcaccc acccaggagt   931
Glu Ser Arg Ile Ser Val Gln Glu Arg Gln
        270                 275 gtggccacgt gggcaaacag gcagttggcc agagagcctg gtgctgctgc tgctgtggcg   991
tgagggtgag gggctggcac tgactgggca tagctcccg cttctgcctg cacccctgca   1051
gtttgagaca ggagacctgg cactggatgc agaaacagtt caccttgaag aacctctcac   1111
ttcaccctgg agcccatcca gtctcccaac ttgtattaaa gacagaggca gaagtttggt   1171
ggtggtggtg ttggggtatg gtttagtaat atccaccaga ccttccgatc cagcagtttg   1231
gtgcccagag aggcatcatg gtggcttccc tgcgcccagg aagccatata cacagatgcc   1291
cattgcagca ttgtttgtga tagtgaacaa ctggaagctg cttaactgtc catcagcagg   1351
agactggcta aataaaatta gaatatattt atacaacaga atctcaaaaa cactgttgag   1411
taaggaaaaa aaggcatgct gctgaatgat gggtatggaa cttttttaaaa aagtacatgc   1471
ttttatgtat gtatattgcc tatggatata tgtataaata caatatgcat catatattga   1531
tataacaagg gttctggaag ggtacacaga aaacccacag ctcgaagagt ggtgacgtct   1591
ggggtgggga agaagggtct ggggg                                         1616

<210> SEQ ID NO 2
<211> LENGTH: 277
<212> TYPE: PRT
<213> ORGANISM: Homo sapiens

<400> SEQUENCE: 2

Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
        195                 200                 205
```

```
Leu Leu Val Leu Val Phe Ile Lys Lys Val Ala Lys Lys Pro Thr Asn
    210                 215                 220
Lys Ala Pro His Pro Lys Gln Glu Pro Gln Glu Ile Asn Phe Pro Asp
225                 230                 235                 240
Asp Leu Pro Gly Ser Asn Thr Ala Ala Pro Val Gln Glu Thr Leu His
                245                 250                 255
Gly Cys Gln Pro Val Thr Gln Glu Asp Gly Lys Glu Ser Arg Ile Ser
            260                 265                 270
Val Gln Glu Arg Gln
        275

<210> SEQ ID NO 3
<211> LENGTH: 43
<212> TYPE: DNA
<213> ORGANISM: Artificial Sequence
<220> FEATURE:
<223> OTHER INFORMATION: Synthetic

<400> SEQUENCE: 3
taggcagtgg tttgacgtcc gcatgttggg aatagccacg cct                 43

<210> SEQ ID NO 4
<211> LENGTH: 49
<212> TYPE: DNA
<213> ORGANISM: Artificial Sequence
<220> FEATURE:
<223> OTHER INFORMATION: Synthetic

<400> SEQUENCE: 4
tagccaaggt aaccagtaca aggtgctaaa cgtaatggct tcggcttac           49

<210> SEQ ID NO 5
<211> LENGTH: 2204
<212> TYPE: DNA
<213> ORGANISM: Homo sapiens
<220> FEATURE:
<221> NAME/KEY: CDS
<222> LOCATION: (156)..(920)

<400> SEQUENCE: 5
ggagccccgg ctcctaggct gacagaccag cccagatcca gtggcccgga ggggcctgag    60
ctaaatccgc aggacctggg taacacgagg aagtcggttt ggtcccttta gggctccgga   120
tatctttggt gacttgtcca ctccagtgtg gcatc atg tgg cag ctg ctc ctc      173
                                      Met Trp Gln Leu Leu Leu
                                        1               5 cca act gct ctg cta ctt cta gtt tca gct ggc atg cgg act gaa gat    221
Pro Thr Ala Leu Leu Leu Leu Val Ser Ala Gly Met Arg Thr Glu Asp
            10                  15                  20 ctc cca aag gct gtg gtg ttc ctg gag cct caa tgg tac agg gtg ctc    269
Leu Pro Lys Ala Val Val Phe Leu Glu Pro Gln Trp Tyr Arg Val Leu
        25                  30                  35 gag aag gac agt gtg act ctg aag tgc cag gga gcc tac tcc cct gag    317
Glu Lys Asp Ser Val Thr Leu Lys Cys Gln Gly Ala Tyr Ser Pro Glu
    40                  45                  50 gac aat tcc aca cag tgg ttt cac aat gag agc ctc atc tca agc cag    365
Asp Asn Ser Thr Gln Trp Phe His Asn Glu Ser Leu Ile Ser Ser Gln
55                  60                  65                  70 gcc tcg agc tac ttc att gac gct gcc aca gtc gac gac agt gga gag    413
Ala Ser Ser Tyr Phe Ile Asp Ala Ala Thr Val Asp Asp Ser Gly Glu
                75                  80                  85 tac agg tgc cag aca aac ctc tcc acc ctc agt gac ccg gtg cag cta    461
Tyr Arg Cys Gln Thr Asn Leu Ser Thr Leu Ser Asp Pro Val Gln Leu
```

```
                      90                  95                 100
gaa gtc cat atc ggc tgg ctg ttg ctc cag gcc cct cgg tgg gtg ttc     509
Glu Val His Ile Gly Trp Leu Leu Leu Gln Ala Pro Arg Trp Val Phe
            105                 110                 115 aag gag gaa gac cct att cac ctg agg tgt cac agc tgg aag aac act     557
Lys Glu Glu Asp Pro Ile His Leu Arg Cys His Ser Trp Lys Asn Thr
        120                 125                 130 gct ctg cat aag gtc aca tat tta cag aat ggc aaa ggc agg aag tat     605
Ala Leu His Lys Val Thr Tyr Leu Gln Asn Gly Lys Gly Arg Lys Tyr
135                 140                 145                 150 ttt cat cat aat tct gac ttc tac att cca aaa gcc aca ctc aaa gac     653
Phe His His Asn Ser Asp Phe Tyr Ile Pro Lys Ala Thr Leu Lys Asp
                155                 160                 165 agc ggc tcc tac ttc tgc agg ggg ctt ttt ggg agt aaa aat gtg tct     701
Ser Gly Ser Tyr Phe Cys Arg Gly Leu Phe Gly Ser Lys Asn Val Ser
            170                 175                 180 tca gag act gtg aac atc acc atc act caa ggt ttg gca gtc tca acc     749
Ser Glu Thr Val Asn Ile Thr Ile Thr Gln Gly Leu Ala Val Ser Thr
        185                 190                 195 atc tca tca ttc ttt cca cct ggg tac caa gtc tct ttc tgc ttg gtg     797
Ile Ser Ser Phe Phe Pro Pro Gly Tyr Gln Val Ser Phe Cys Leu Val
200                 205                 210 atg gta ctc ctt ttt gca gtg gac aca gga cta tat ttc tct gtg aag     845
Met Val Leu Leu Phe Ala Val Asp Thr Gly Leu Tyr Phe Ser Val Lys
215                 220                 225                 230 aca aac att cga agc tca aca aga gac tgg aag gac cat aaa ttt aaa     893
Thr Asn Ile Arg Ser Ser Thr Arg Asp Trp Lys Asp His Lys Phe Lys
                235                 240                 245 tgg aga aag gac cct caa gac aaa tga cccccatccc atggggtaa            940
Trp Arg Lys Asp Pro Gln Asp Lys
            250 taagagcagt agcagcagca tctctgaaca tttctctgga tttgcaaccc catcatcctc   1000
aggcctctct acaagcagca ggaaacatag aactcagagc cagatccctt atccaactct   1060
cgactttcc ttggtctcca gtggaaggga aaagcccatg atcttcaagc agggaagccc    1120
cagtgagtag ctgcattcct agaaattgaa gtttcagagc tacacaaaca cttttctgt    1180
cccaaccgtt ccctcacagc aaagcaacaa tacaggctag ggatggtaat cctttaaaca   1240
tacaaaaatt gctcgtgtta taaattaccc agtttagagg ggaaaaaaaa acaattattc   1300
ctaaataaat ggataagtag aattaatggt tgaggcagga ccatacagag tgtgggaact   1360
gctgggatc tagggaattc agtgggacca atgaaagcat ggctgagaaa tagcaggtag    1420
tccaggatag tctaagggag gtgttcccat ctgagcccag agataagggt gtcttcctag   1480
aacattagcc gtagtggaat taacaggaaa tcatgagggt gacgtagaat tgagtcttcc   1540
aggggactct atcagaactg gaccatctcc aagtatataa cgatgagtcc tcttaatgct   1600
aggagtagaa aatggtccta ggaaggggac tgaggattgc ggtgggggt ggggtggaaa    1660
agaaagtaca gaacaaaccc tgtgtcactg tcccaagttg ctaagtgaac agaactatct   1720
cagcatcaga atgagaaagc ctgagaagaa agaaccaacc acaagcacac aggaaggaaa   1780
gcgcaggagg tgaaaatgct tccttggcca gggtagtaag aattagaggt taatgcaggg   1840
actgtaaaac cacctttctt gcttcaatat ctaattcctg tgtagctttg ttcattgcat   1900
ttattaaaca aatgttgtat aaccaatact aaatgtacta ctgagcttcg ctgagttaag   1960
ttatgaaact ttcaaatcct tcatcatgtc agttccaatg aggtgggat ggagaagaca    2020
attgttgctt atgaaagaaa gctttagctg tctctgtttt gtaagcttta agcgcaacat   2080
```

```
ttcttggttc aataaagca ttttacaaga tcttgcatgc tactcttaga tagaagatgg   2140 gaaaccatg gtaataaaat atgaatgata aaaaaaaaaa aaaaaaaaaa aaaaaaaaaa   2200
aaaa                                                               2204
```

<210> SEQ ID NO 6
<211> LENGTH: 254
<212> TYPE: PRT
<213> ORGANISM: Homo sapiens

<400> SEQUENCE: 6

```
Met Trp Gln Leu Leu Pro Thr Ala Leu Leu Leu Val Ser Ala
 1               5                  10                  15

Gly Met Arg Thr Glu Asp Leu Pro Lys Ala Val Val Phe Leu Glu Pro
                20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Phe
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Phe Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250
```

<210> SEQ ID NO 7
<211> LENGTH: 40
<212> TYPE: DNA
<213> ORGANISM: Artificial Sequence
<220> FEATURE:
<223> OTHER INFORMATION: Synthetic

<400> SEQUENCE: 7

```
gctagtcaga tcgtaggtag accacgacga cacaccctaa                          40
```

<210> SEQ ID NO 8
<211> LENGTH: 45
<212> TYPE: DNA
<213> ORGANISM: Artificial Sequence
<220> FEATURE:

```
<223> OTHER INFORMATION: Synthetic

<400> SEQUENCE: 8
gctagtcaga tcgtaggtag tttttaccac gacgacacac cctaa            45
```